(12) United States Patent
Shimuta

(10) Patent No.: US 10,149,623 B2
(45) Date of Patent: Dec. 11, 2018

(54) PULSE WAVE SENSOR DEVICE

(71) Applicant: MURATA MANUFACTURING CO., LTD., Nagaokakyo-Shi, Kyoto-fu (JP)

(72) Inventor: Toru Shimuta, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 963 days.

(21) Appl. No.: 14/091,132

(22) Filed: Nov. 26, 2013

(65) Prior Publication Data
US 2014/0088396 A1 Mar. 27, 2014

Related U.S. Application Data

(63) Continuation of application No. PCT/JP2012/060125, filed on Apr. 13, 2012.

(30) Foreign Application Priority Data

May 31, 2011 (JP) .................................. 2011-121922
Aug. 19, 2011 (JP) .................................. 2011-179553

(51) Int. Cl.
*A61B 5/024* (2006.01)
*A61B 5/0245* (2006.01)
(Continued)

(52) U.S. Cl.
CPC ........ *A61B 5/02427* (2013.01); *A61B 5/0245* (2013.01); *A61B 5/6806* (2013.01);
(Continued)

(58) Field of Classification Search
CPC ............ A61B 5/02416; A61B 5/02422; A61B 5/02427; A61B 5/6806; A61B 5/6898;
(Continued)

(56) References Cited

U.S. PATENT DOCUMENTS 4,378,111 A * 3/1983 Tsuchida ................ A63B 24/00
482/54
5,735,799 A * 4/1998 Baba ..................... A61B 5/021
600/485
(Continued)

FOREIGN PATENT DOCUMENTS

CN 101810470 A 8/2010
JP S61-48338 A 3/1986
(Continued)

OTHER PUBLICATIONS

PCT/JP2012/060125, International Search Report, dated Jun. 6, 2012.
(Continued)

*Primary Examiner* — Meredith Weare
(74) *Attorney, Agent, or Firm* — Arent Fox LLP

(57) ABSTRACT

A light emitter and a light receiver are provided at a side surface of a lever. When a user grips the lever with his hand, the light emitter and the light receiver are positioned close to bases of the middle finger, a ring finger, and a little finger, as a measurement portion of a palm. A blood-flow blockage reducing component protrudes to contact a portion between the index finger and the middle finger, and a thumb, as a contact portion of the palm.

15 Claims, 19 Drawing Sheets

(51) Int. Cl.
  *A61B 5/00* (2006.01)
  *A61B 5/0404* (2006.01)
  *A61B 5/1455* (2006.01)

(52) U.S. Cl.
  CPC .......... *A61B 5/6898* (2013.01); *A61B 5/0404* (2013.01); *A61B 5/14552* (2013.01); *A61B 5/6825* (2013.01); *A61B 5/6897* (2013.01)

(58) Field of Classification Search
  CPC . A61B 5/0245; A61B 5/14552; A61B 5/0404; A61B 5/6897; A61B 5/6825
  See application file for complete search history.

(56) References Cited

U.S. PATENT DOCUMENTS

| | | | |
|---|---|---|---|
| 5,990,866 A * | 11/1999 | Yollin | A63F 13/06 345/157 |
| 7,149,571 B2 | 12/2006 | Maeda | |
| 7,197,351 B2 | 3/2007 | Umeda et al. | |
| 7,869,849 B2 * | 1/2011 | Ollerdessen | A61B 5/14552 600/323 |
| 2003/0036685 A1 * | 2/2003 | Goodman | A61B 5/0002 600/300 |
| 2008/0076982 A1 * | 3/2008 | Ollerdessen | A61B 5/14552 600/310 |
| 2008/0238695 A1 * | 10/2008 | Yanai | A61B 5/02427 340/576 |
| 2008/0293491 A1 * | 11/2008 | Wu | A63F 13/06 463/37 |
| 2009/0015558 A1 * | 1/2009 | Hung | A61B 5/02433 345/163 |
| 2009/0227852 A1 * | 9/2009 | Glaser | A42B 3/0433 600/324 |
| 2009/0247885 A1 * | 10/2009 | Suzuki | A61B 5/02416 600/500 |
| 2010/0292589 A1 * | 11/2010 | Goodman | A61B 5/021 600/500 |

FOREIGN PATENT DOCUMENTS

| | | | |
|---|---|---|---|
| JP | S63-71236 A | | 3/1988 |
| JP | 06-22914 | | 2/1994 |
| JP | 07-115677 A | | 2/1995 |
| JP | 08-66378 A | | 3/1996 |
| JP | 3303299 B2 | | 7/2002 |
| JP | 2002-282226 A | | 10/2002 |
| JP | 2003-144403 A | | 5/2003 |
| JP | 2004-000467 A | | 1/2004 |
| JP | 2005-046215 A | | 2/2005 |
| JP | 2005-160621 A | | 6/2005 |
| JP | 2006-022914 A | | 1/2006 |
| JP | 2006-026211 A | | 2/2006 |
| JP | 2006-158974 A | | 6/2006 |
| JP | 2007-313358 A | | 12/2007 |
| JP | 2008-048987 A | | 3/2008 |
| JP | 2008-237378 A | | 10/2008 |
| JP | 2008-272082 A | | 11/2008 |
| JP | 2009-006113 A | | 1/2009 |
| JP | 2009-034398 A | | 2/2009 |
| JP | 2009-034398 A * | 2/2009 | ........... A61B 5/0245 |
| WO | WO-1994-015525 A1 | | 7/1994 |

OTHER PUBLICATIONS

PCT/JP2012/060125, Written Opinion of the International Searching Authority, dated Jun. 6, 2012.

* cited by examiner

PULSE WAVE SENSOR DEVICE

CROSS REFERENCE TO RELATED APPLICATIONS

The present application is a continuation of PCT/JP2012/060125 filed Apr. 13, 2012, which claims priority to Japanese Patent Application No. 2011-121922, filed May 31, 2011, and to Japanese Patent Application No. 2011-179533, filed Aug. 19, 2011, the entire contents of each of which are incorporated herein by reference.

FIELD OF THE INVENTION

The present invention relates to a pulse wave sensor device that irradiates a hand with light and detects a pulse wave.

BACKGROUND OF THE INVENTION

A generally known pulse wave sensor device includes a light emitter that irradiates a finger with light and a light receiver that receives light reflected by the finger, and detects a pulse wave based on a change in quantity of light between the light emitted from the light emitter and the light received by the light receiver (for example, see Patent Documents 1 to 3).

When a finger is strongly pressed to the light emitter or the light receiver, the finger is compressed and blood flow in arteries is blocked. Hence, a pulse wave signal becomes weak and the pulse wave is no longer detected. With regard to this, Patent Document 1 discloses a configuration in which pressing force detecting means for detecting a pressing force of a finger is provided, and a function of informing a user if the pressing force is strong is added.

Also, Patent Documents 2 and 3 disclose a configuration in which a light emitter is provided to protrude with respect to the periphery of the light emitter to allow the light emitter to reliably contact a finger, so that a pulse wave can be easily detected.

Patent Document 1: International Publication No. 94/015525

Patent Document 2: Japanese Unexamined Patent Application Publication No. 2004-000467

Patent Document 3: Japanese Unexamined Patent Application Publication No. 2008-048987

The pulse wave sensor device in Patent Document 1 has the function of informing the user about that measurement cannot be performed because the pressing force of the finger is too strong. However, with this configuration, even when the pressing force of the finger is strong and measurement cannot be performed, only the information is only provided. Owing to this, to perform measurement for a certain time, the pressing force of the finger has to be held stably in a weak state, and thus the user is forced to bear the burden.

Also, Patent Documents 2 and 3 disclose the configuration in which the light emitter is provided to protrude with respect to the periphery of the light emitter to allow the light emitter to reliably contact the finger. However, the configuration does not reduce the pressing force of the finger, the situation, in which the pulse wave cannot be detected if the pressing force of the finger is too strong, is not changed, and hence a problem similar to the above-described problem arises.

SUMMARY OF THE INVENTION

The present invention is made to address the problem, and an object of the invention is to provide a pulse wave sensor device that can easily detect a pulse wave by reducing blockage of blood flow.

(1) To address the above-described problem, the invention provides a pulse wave sensor device including a light emitter that outputs light to a living body, and a light receiver that receives light, which is emitted from the light emitter and reflected by the living body, the pulse wave sensor device configured to detect a pulse wave. The light emitter and the light receiver are arranged in a measurement portion, which excludes a center portion and a wrist-side portion of a palm of the living body, and in which the pulse wave is measured. A blood-flow blockage reducing part is provided, when the measurement portion of the palm is arranged at the light emitter and the light receiver, the blood-flow blockage reducing part contacting a portion, which excludes the center portion and the wrist-side portion of the palm, and which is the same as the measurement portion, or which is different from the measurement portion. A step is formed around the blood-flow blockage reducing part.

In a case in which a pulse wave is detected by using a fingertip, if the finger is strongly compressed, blood flow is blocked, and the pulse wave is no longer detected. Also, for example, when a hand performs various operations or physical activity, a finger frequently moves, and hence the pulse wave becomes less likely stable.

Regarding these points, with the invention, the light emitter and the light receiver are arranged at the positions so as to face the palm, and the pulse wave of the palm is detected. Accordingly, even when the finger moves, the blood flow of the palm at the upstream side becomes relatively stable, and the pulse wave can be stably detected.

Also, in a hand of a living body, arteries form arches at a center portion of a palm and then arteries are spread to the respective fingers. Hence, if the center portion or a wrist-side portion of the palm are strongly compressed, the blood flow of the palm may be blocked.

In contrast, with the invention, the light emitter and the light receiver are arranged at the measurement portion, which excludes the center portion and the wrist-side portion of the palm and in which the pulse wave is measured. Also, the blood-flow blockage reducing part that contacts the portion, which excludes the center portion and the wrist-side portion of the palm, and which is the same as the measurement portion, or which is different from the measurement portion, is provided.

Hence, when the user of the pulse wave sensor device arranges the measurement portion of the palm at the light emitter and the light receiver, the portion excluding the center portion and the wrist-side portion of the palm contacts the blood-flow blockage reducing part. At this time, since the step is formed around the blood-flow blockage reducing part, the compression acting on a portion at an upstream side of blood flow with respect to the measurement portion of the palm can be reduced. The portion at the upstream side is the center portion or the wrist-side portion of the palm, for example. Consequently, even if the palm is strongly pressed to the light emitter and the light receiver, the blood flow is not blocked in the measurement portion, the burden of the user is reduced, and the pulse wave can be easily detected.

(2) In the invention, the step formed around the blood-flow blockage reducing part may reduce compression acting on a portion at an upstream side of blood flow with respect to the measurement portion of the palm, and reduce blockage of the blood flow in the measurement portion. Accordingly, the blockage of the blood flow in the measurement portion of the palm is reduced, and the pulse wave can be easily detected.

(3) In the invention, the measurement portion may be a portion close to a base of a finger with respect to the center portion of the palm. Accordingly, for example, when the light emitter and the light receiver are attached to a configuration with a shape that is gripped with a hand, the light emitter and the light receiver can easily approach the portion close to the base of the finger serving as the measurement portion.

(4) In the invention, the light emitter and the light receiver may be attached to a lever that is operated while the lever is gripped with a hand. The blood-flow blockage reducing part may contact a portion between an index finger and a middle finger, and a thumb of the palm.

In this case, since the light emitter and the light receiver are attached to the lever, when the lever is gripped with the hand, the light emitter and the light receiver are arranged at the measurement portion of the palm, and the blood-flow blockage reducing part contacts the portion between the index finger and the middle finger, and the thumb of the palm. Accordingly, even when the user strongly grips the lever, the step is formed around the blood-flow blockage reducing part, the compression on the center portion and the wrist-side portion of the palm is reduced, the blood-flow blockage can be restricted, and the pulse wave can be stably detected. Also, since the measurement portion is close to the base of the finger with respect to the center portion, even when the fingertip moves by the operation of the lever, the influence on the blood flow in the measurement portion can be reduced. Accordingly, even when the lever is operated, the pulse wave can be stably detected.

(5) In the invention, the lever may include a left-hand lever and a right-hand lever, and the light emitter and the light receiver may be attached to the left-hand lever at positions different from positions of the light emitter and the light receiver attached to the right-hand lever.

Accordingly, even if the size of the palm varies depending on the user of the pulse wave sensor, for example, in a case of an adult and a child, the light emitter and the light receiver can be brought into contact with the proper measurement portion of the palm by using at least one of the left-hand lever and the right-hand lever.

(6) In the invention, the light emitter and the light receiver may be attached to an operation device that is operated with a fingertip while the operation device is gripped with a hand. The blood-flow blockage reducing part may contact a portion between an index finger and a middle finger, and a thumb of the palm.

With the invention, since the light emitter and the light receiver are attached to the operation device, when the operation device is held with the hand, the light emitter and the light receiver are arranged at the measurement portion of the palm, and the blood-flow blockage reducing part contacts the portion between the index finger and the middle finger, and the thumb of the palm. Accordingly, even when the user strongly grips the operation device, the step is formed around the blood-flow blockage reducing part, the compression on the center portion and the wrist-side portion of the palm is reduced, the blood-flow blockage can be restricted, and the pulse wave can be stably detected. Also, since the measurement portion is close to the base of the finger with respect to the center portion of the palm, even when the operation device is operated with the fingertip, the influence on the blood flow in the measurement portion is reduced. Accordingly, even when the operation device is operated, the pulse wave can be stably detected.

(7) In the invention, the measurement portion may be a hypothenar of the palm. In this case, since the hypothenar of the palm is softer than the other portion, even when a sensor casing strongly contacts the hypothenar of the palm, the blood flow is less likely blocked. Also, even when the hand is closed, a fingertip hardly contacts the hypothenar of the palm. The sensor casing less likely becomes an obstruction although the sensor casing is attached in contact with the hypothenar. Accordingly, even during physical activity, the pulse wave can be stably detected.

(8) In the invention, the light emitter and the light receiver may be housed in a sensor casing. The sensor casing may be attached to a fixing tool that is worn on a hand in a state in which the sensor casing contacts the hypothenar of the palm. The sensor casing may protrude to the palm with respect to the fixing tool, and form the blood-flow blockage reducing part.

With the invention, since the sensor casing is attached to the fixing tool worn on the hand in the state in which the sensor casing contacts the hypothenar of the hand, the light emitter and the light receiver housed in the sensor casing may approach the hypothenar of the palm being the measurement portion. Also, since the sensor casing protrudes to the palm with respect to the fixing tool, the sensor casing can contact the hypothenar of the palm before the fixing tool, and a step can be formed around the sensor casing. Accordingly, the sensor casing can form the blood-flow blockage reducing part. The compression acting on the center portion and the wrist-side portion of the palm, which are the portions at the upstream side of the blood flow with respect to the measurement portion, is reduced, and hence the pulse wave can be stably detected.

(9) In the invention, the light emitter and the light receiver may be housed in a sensor casing. The sensor casing may be attached to a fixing tool that is worn on a hand in a state in which the sensor casing contacts a portion close to a base of a finger with respect to the center portion of the palm. The sensor casing may protrude to the palm with respect to the fixing tool, and form the blood-flow blockage reducing part.

With the invention, since the sensor casing is attached to the fixing tool worn on the hand in the state in which the sensor casing contacts the portion close to the base of the finger with respect to the center portion of the hand, the light emitter and the light receiver housed in the sensor casing may approach the portion close to the base of the finger of the palm being the measurement portion. Also, since the sensor casing protrudes to the palm with respect to the fixing tool, the sensor casing can contact the portion close to the base of the finger of the palm before the fixing tool, and a step can be formed around the sensor casing. Accordingly, the sensor casing can form the blood-flow blockage reducing part. The compression acting on the center portion and the wrist-side portion of the palm, which are the portions at the upstream side of the blood flow with respect to the measurement portion, is reduced, and hence the pulse wave can be stably detected. Further, if the sensor casing is arranged at the position close to the base of the ring finger of the palm and the blood-flow blockage reducing part that contacts the portion between the index finger and the middle finger, and the thumb of the palm is additionally provided, the pulse wave can be further stably detected.

(10) The invention may further include an electrocardiograph electrode for contacting a hand of the living body and measuring an electrocardiograph signal.

Accordingly, the electrocardiograph signal by using the electrocardiograph electrode and the photoelectric pulse wave signal can be simultaneously measured. Thus, living body information, such as an electrocardiogram, a heart rate (pulse rate), oxygen saturation, a pulse wave propagation time, an acceleration pulse wave, and pulse fluctuation, can be generated based on the photoelectric pulse wave signal and the electrocardiograph signal.

(11) In the invention, the electrocardiograph electrode may be arranged at least at one of a surface position of the blood-flow blockage reducing part, a position at which the electrocardiograph electrode contacts between an index finger and a thumb of the palm, and a position at which the electrocardiograph electrode contacts a hypothenar of the palm.

Accordingly, the electrocardiograph electrode can be attached at the position so as to stably contact the hand of the user. Consequently, since noise that is generated if a finger moves is less superposed on the electrocardiograph signal, the electrocardiograph signal can be stably measured.

(12) The invention may further include a ground electrode that is arranged at a position different from the position of the electrocardiograph electrode and connected with a ground potential, the ground electrode being arranged at least at one of a surface position of the blood-flow blockage reducing part, a position at which the ground electrode contacts between an index finger and a thumb of the palm, and a position at which the ground electrode contacts a hypothenar of the palm.

Accordingly, the ground potential can be aligned with the user (living body). Hence, even if noise, such as commercial power noise, is mixed through the user, the electrocardiograph signal can be stably measured.

DETAILED DESCRIPTION OF THE PREFERRED EMBODIMENTS OF THE INVENTION

Figure 1:
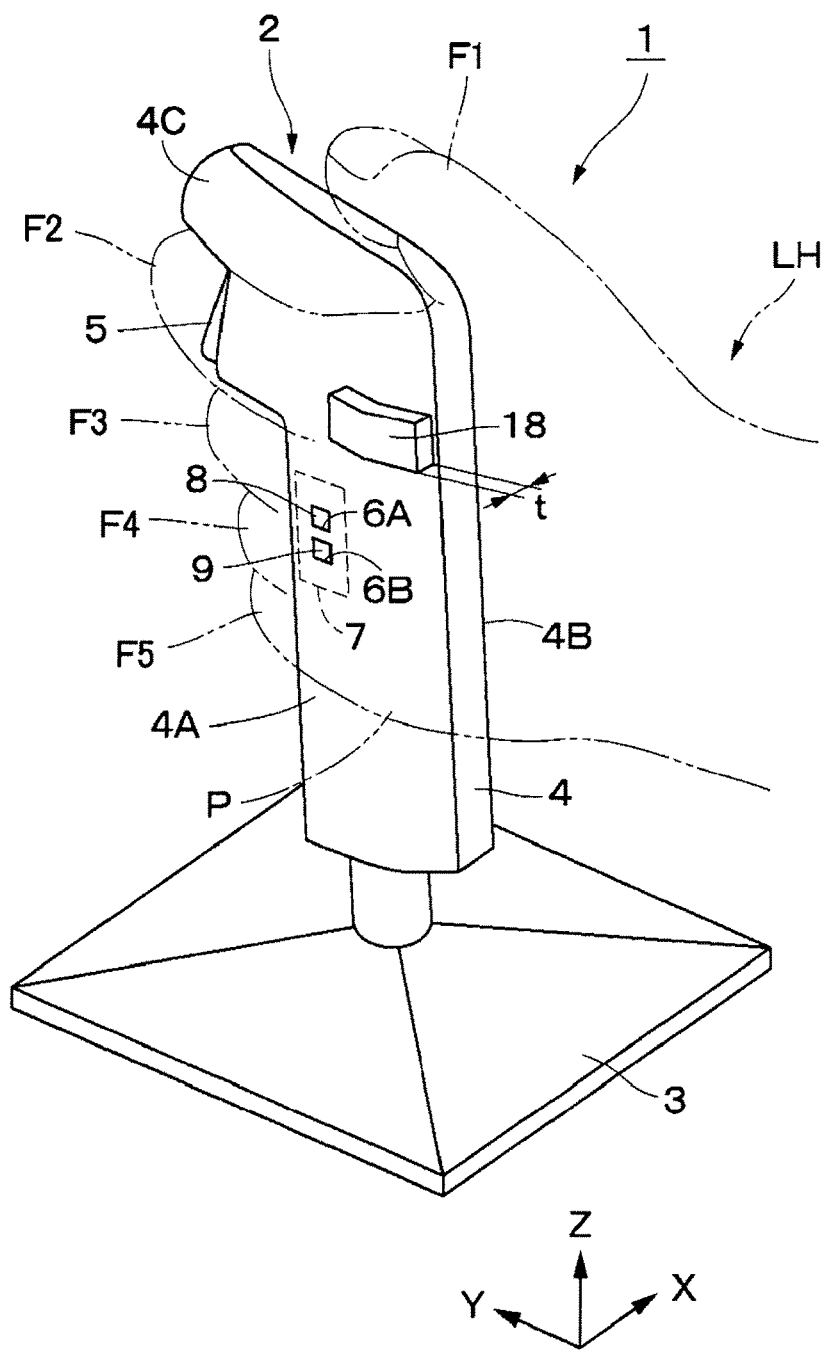
FIG. 1 is a perspective view from the left side of a pulse wave sensor device according to a first embodiment.

Pulse wave sensor devices according to embodiments of the invention are described below with reference to the accompanying drawings. For the convenience of description, it is assumed that the X direction in FIG. 1 represents the left-right direction, the Y direction represents the front-rear direction, and the Z direction represents the up-down direction. Also, the description is given with an example in which a pulse wave is measured by using a left hand LH.

Figure 2:
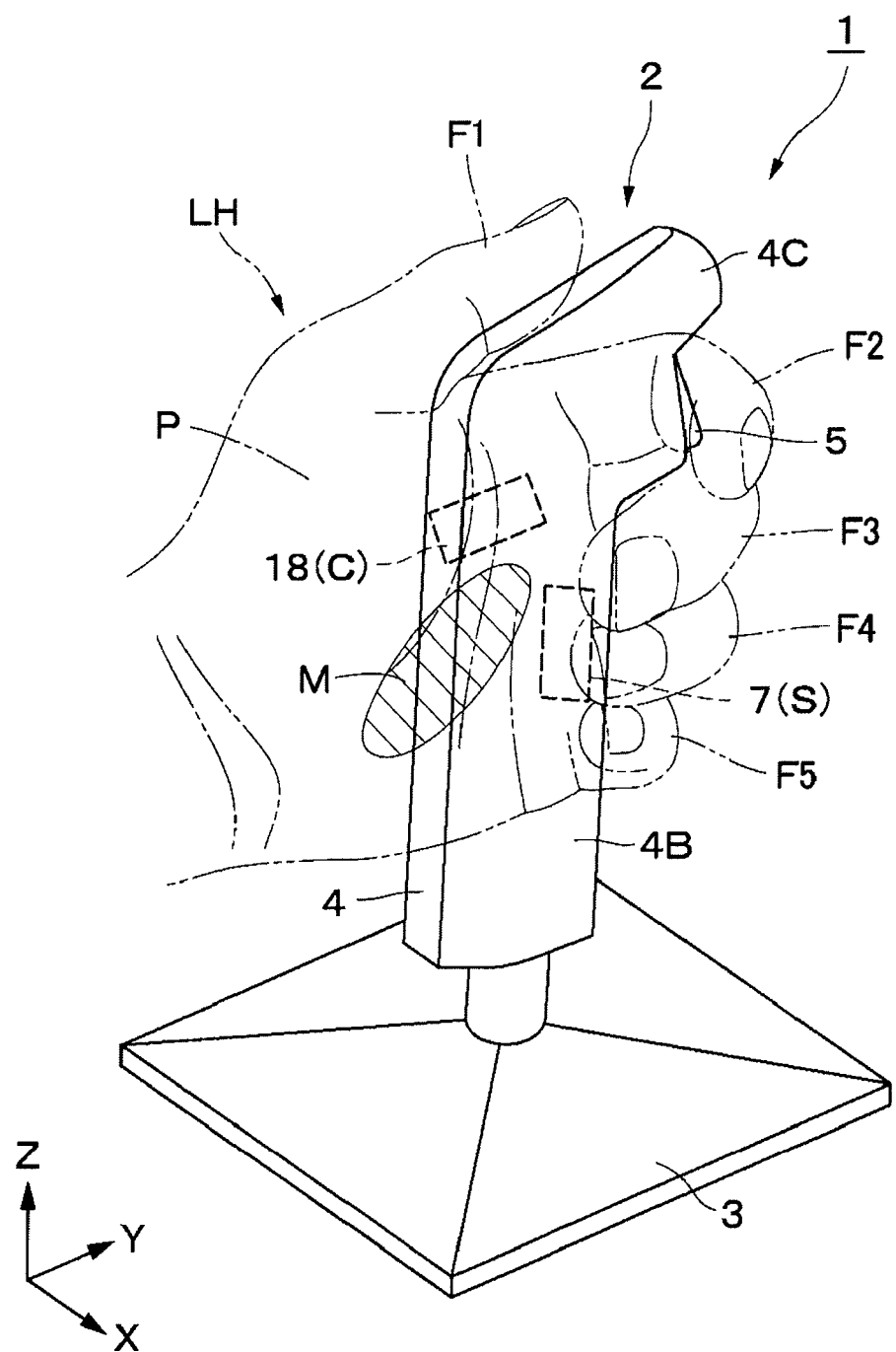
FIG. 2 is a perspective view from the right side of the pulse wave sensor device in FIG. 1.
Figure 3:
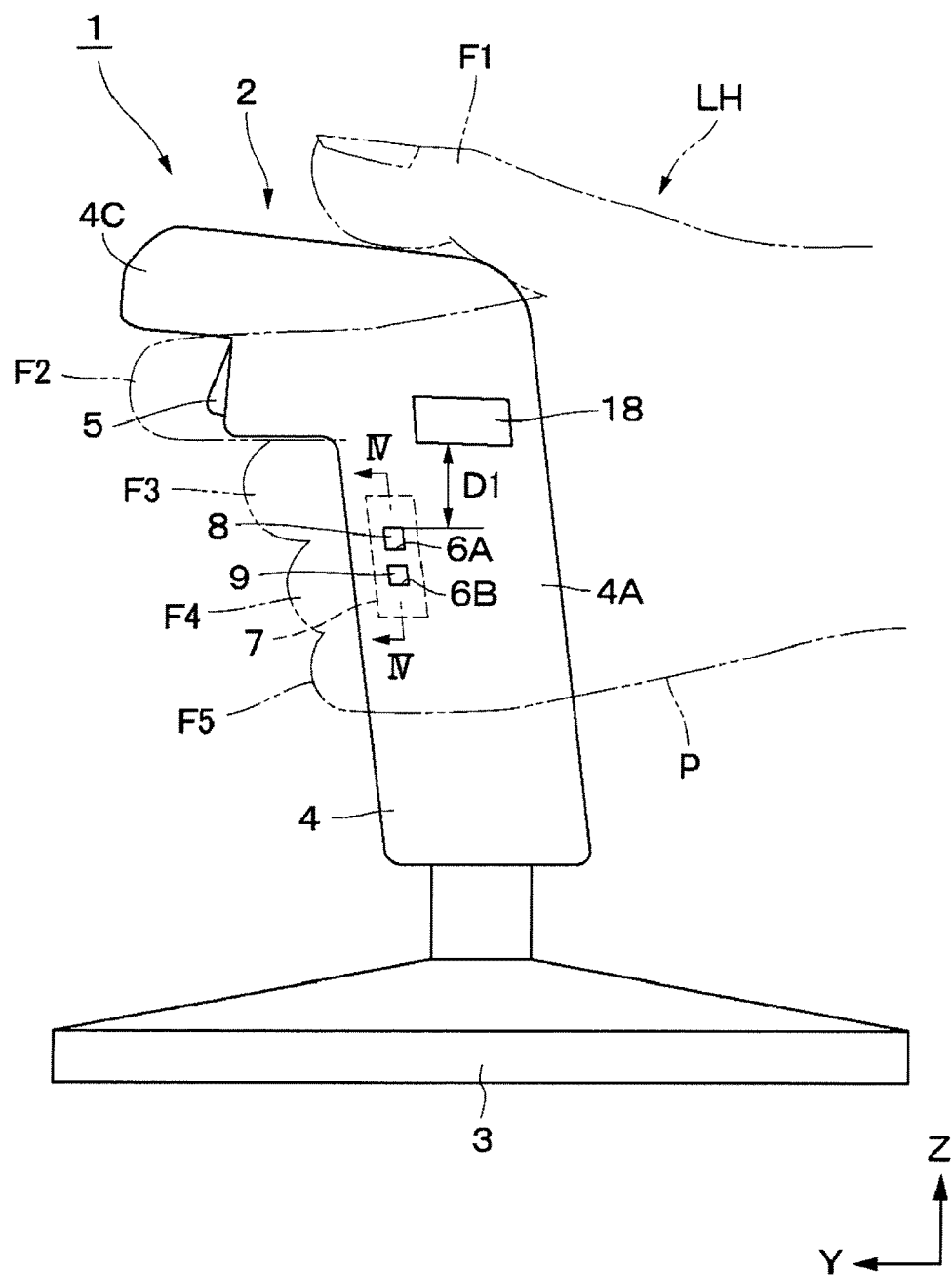
FIG. 3 is a front view of the pulse wave sensor device in FIG. 1.

FIGS. 1 to 3 illustrate a pulse wave sensor device 1 according to a first embodiment. For example, the pulse wave sensor device 1 is applied to a lever device 2 that operates an operation subject in a game screen. The pulse wave sensor device 1 detects a photoelectric pulse wave signal (pulse wave signal) corresponding to a pulse wave from a palm P. Based on the photoelectric pulse wave signal, the pulse wave sensor device 1 can generate living body information, such as oxygen saturation, an acceleration pulse wave, and pulse fluctuation, and can further estimate an autonomic nervous condition.

The lever device 2 includes a pedestal 3 and a lever 4 serving as a control stick and attached to the pedestal 3 so as to be tilted. The pedestal 3 is formed in a flat plate shape expanding in, for example, the X and Y directions. A center portion of the pedestal 3 is bulged upward. The lever 4 forms a sensor attachment body, is formed in a rod-like or cylinder-like shape extending in the Z direction, and is supported by the pedestal 3 at the lower end of the lever 4. The lever 4 has a shape that allows a user to grip the lever 4 with the left hand LH. To prevent the lever 4 from being operated with the right hand, for example, the outer peripheral surface of the lever 4 may have recesses or protrusions to guide the thumb F1, the index finger F2, the middle finger F3, the ring finger F4, and the little finger F5 of the left hand LH.

In this case, the lever 4 is attached to the pedestal 3 by using, for example, a universal joint, and hence the lever 4 can be tilted in any direction of the X and Y directions. Also, the pedestal 3 is provided with a sensor (not illustrated) that detects the tilt direction and the tilt angle of the lever 4.

The lever 4 has a left side surface 4A and a right side surface 4B, and a trigger button 5 at the front side of the lever 4. A guide protrusion 4C protruding forward is formed above the trigger button 5. The index finger F2 of the left hand LH is guided to the position of the trigger button 5 by the guide protrusion 4C. Thus, the user can hold the lever 4 while hooking the index finger F2 of the left hand LH to the trigger button 5, and can perform a pressing operation on the trigger button 5 by gripping the index finger F2. A button (not illustrated) operable with the thumb F1 may be provided at the upper surface or the rear surface of the lever 4. Also, the trigger button 5 does not have to be provided at the lever 4, and may be omitted.

The pedestal 3 of the lever device 2 is provided with a signal output circuit (not illustrated) that outputs a signal from the sensor that detects the tilt direction etc. of the lever 4 and a signal from the trigger button 5. Also, the lever device 2 is connected with, for example, a game machine or a computer by a wired method or a wireless method. The lever device 2 functions as a game controller. The lever device 2 outputs a signal corresponding to the tilt direction and the tilt angle of the lever 4 and a signal corresponding to the pressing operation of the trigger button 5. For example, the operation subject in the game screen on a monitor (not illustrated) performs various actions, such as moving, turning, jumping, and shooting, in accordance with the signals.

Figure 4:
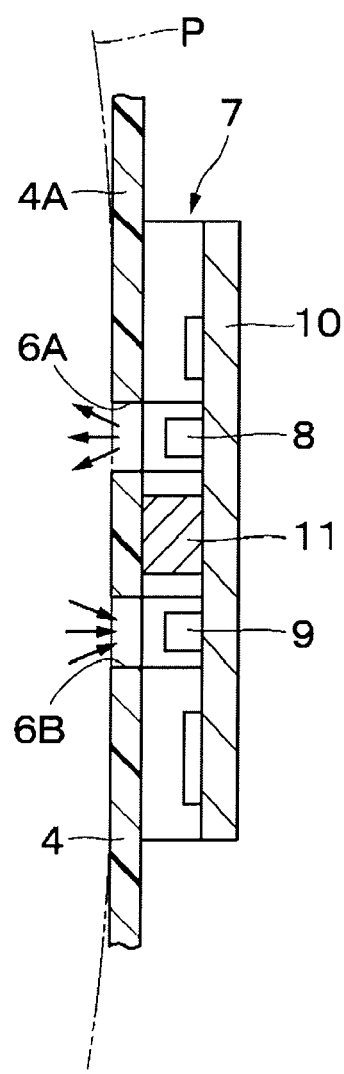
FIG. 4 is a cross-sectional view of a light emitter, a light receiver, and other parts of the pulse wave sensor device taken along arrow IV-IV in FIG. 3.

A sensor unit 7 is attached to the left side surface 4A of the lever 4. The sensor unit 7 includes a light emitter 8 and a light receiver 9. To be specific, the left side surface 4A of the lever 4 has two element openings 6A and 6B having small opening areas. The light emitter 8 and the light receiver 9 are attached to the element openings 6A and 6B, respectively. Also, as illustrated in FIG. 4, a substrate 10 is housed in the lever 4 at a position so as to face the two element openings 6A and 6B. The substrate 10 is fitted to, for example, an attachment part (not illustrated) of the lever 4, and hence is fixed to the lever 4. The light emitter 8 and the light receiver 9 are mounted on the substrate 10.

The light emitter 8 is formed, for example, by sealing a light-emitting element such as a light-emitting diode (LED) with transparent resin. The light emitter 8 irradiates the palm P of the left hand LH of the user of the pulse wave sensor device 1 with light having a predetermined wavelength (for example, visible light or infrared light). Alternatively, the light emitter 8 may be formed by using a surface emitting laser (vertical cavity surface emitting laser, VCSEL) or a resonator LED as the light-emitting element.

Also, the light emitter 8 is arranged at a position to face the element opening 6A so that the light emitter 8 can output the light to the palm P through the element opening 6A. For example, the surface of the light emitter 8 may be arranged to be aligned with the left side surface 4A of the lever 4 or may be arranged to protrude from the left side surface 4A so that the light emitter 8 contacts the left hand LH of the user. Alternatively, the surface of the light emitter 8 may be arranged in a recessed manner. The light emitter 8 is driven by a light-emitter driver 14 (described later).

When the light emitter 8 irradiates the palm P of the left hand LH with the light as described above, the light receiver 9 receives reflection light from the palm P, converts the reflection light into a light detection signal, and outputs the light detection signal to a light-detection-signal amplifier 15 of a processing circuit 12. The light receiver 9 is formed, for example, by sealing a light-receiving element such as a photodiode (PD) with transparent resin. Alternatively, the light receiver 9 may be formed by using, for example, a phototransistor as the light-receiving element.

Also, the light receiver 9 is arranged at a position to face the element opening 6B so that the light receiver 9 can receive the light from the palm P through the element opening 6B. For example, the surface of the light receiver 9 may be arranged to be aligned with the left side surface 4A of the lever 4 or may be arranged to protrude from the left side surface 4A so that the light receiver 9 contacts the palm P of the left hand LH of the user. Alternatively, the surface of the light receiver 9 may be arranged in a recessed manner. That is, the light emitter 8 and the light receiver 9 may contact the palm P, or may be separated from the palm P in a range that allows a photoelectric pulse wave to be detected. To prevent external light from being mixed, peripheral portions of the light emitter 8 and the light receiver 9 of the lever 4, that is, peripheral edge portions of the element openings 6A and 6B of the lever 4 preferably contact the palm P, so that the peripheries of the light emitter 8 and the light receiver 9 are shielded from light.

The light emitter 8 and the light receiver 9 are arranged at a measurement portion S of the palm P of the left hand LH. The measurement portion S excludes a center portion M and a wrist-side portion W of the palm P. A pulse wave is measured at the measurement portion S. In this case, the measurement portion S is a portion close to the base of a finger with respect to the center portion M of the palm P.

The index finger F2 moves by the operation of the trigger button 5. Also, the thumb F1 likely moves by the operation of the lever 4. If the fingers F1 and F2 move, the contact state between the lever 4 and the skin and the blood flow in the base portion may likely vary. Owing to this, the measurement portion S is preferably a portion of the palm P close to the bases of the residual three fingers F3 to F5 excluding the thumb F1 and the index finger F2. To be more specific, the measurement portion S is preferably a portion in a range extending from a palmophalangeal crease PC, which is located at the base of the ring finger F4, to an area close to a distal palmar crease DPC of the palm P. The area close to the distal palmar crease DPC includes the distal palmar crease DPC.

In particular, if the measurement portion S is set at the portion close to the base of the ring finger F4, when the lever 4 is gripped with the left hand LH, the pulse wave can be measured while the light emitter 8 and the light receiver 9 spontaneously closely face the measurement portion S. In addition, even when the lever 4 or the trigger button 5 is operated, the ring finger F4 move less, and hence the pulse wave can be stably detected.

Also, when the user grips the lever 4 with the left hand LH, the index finger F2 is hooked to the trigger button 5. Accordingly, since the position of the base of the index finger F2 can be expected with the trigger button 5, the light emitter 8 and the light receiver 9 are positioned at a lower portion of the lever 4 with respect to the trigger button 5, and are arranged at positions with regard to the average size of the palm P.

The distance between the light emitter 8 and the light receiver 9 is set, for example, within a range from 4 to 20 mm. Also, a light-shielding part 11 is provided between the light emitter 8 and the light receiver 9. The light-shielding part 11 is made of, for example, an optically opaque resin material so that the light receiver 9 does not directly receive the light emitted from the light emitter 8. The light receiver 9 may be arranged at any position as long as the light receiver 9 is provided around the light emitter 8.

Figure 5:
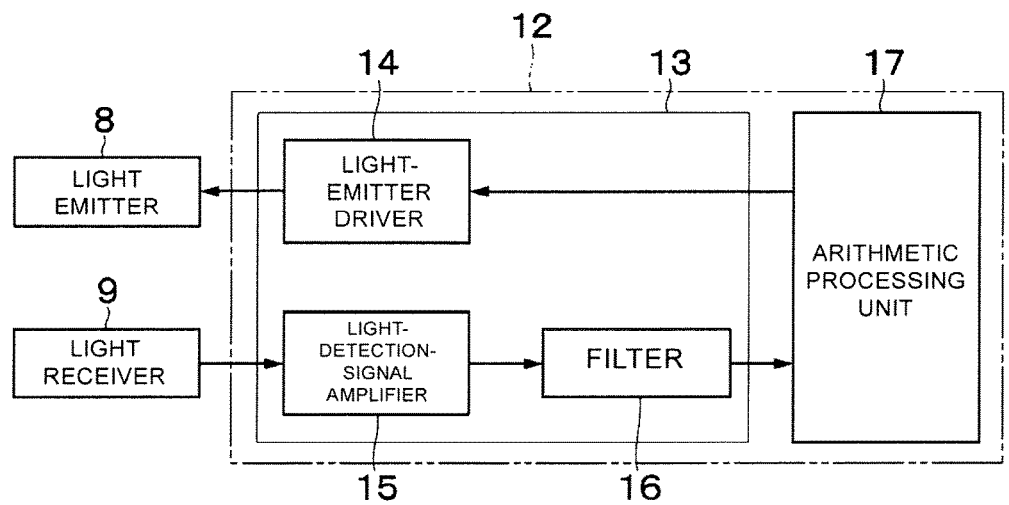
FIG. 5 is a block diagram illustrating an electric configuration of the pulse wave sensor device according to the first embodiment.

As illustrated in FIG. 5, the processing circuit 12 mainly includes a photoelectric-pulse-wave-signal detector 13 and an arithmetic processing unit 17. For example, the processing circuit 12 is provided in the lever 4.

The photoelectric-pulse-wave-signal detector 13 includes the light-emitter driver 14, the light-detection-signal amplifier 15, and a filter 16, and generates a photoelectric pulse wave signal of the user in association with the arithmetic processing unit 17. The light-emitter driver 14 is connected with the light emitter 8 and supplies driving current to cause the light emitter 8 to emit light. The light-detection-signal amplifier 15 is connected with the light receiver 9, performs current-voltage transformation on a light detection signal supplied from the light receiver 9, and amplifies the light detection signal after the current-voltage transformation. The filter 16 is formed of, for example, a low pass filter, is connected to the downstream side of the light-detection-signal amplifier 15, and removes noise from the light detection signal output from the light-detection-signal amplifier 15.

The photoelectric-pulse-wave-signal detector 13 drives the light emitter 8 by using the light-emitter driver 14, and outputs the light detection signal corresponding to the reflection light from the palm P to the arithmetic processing unit 17 by using the light-detection-signal amplifier 15 and the filter 16.

The arithmetic processing unit 17 is, for example, a central processing unit (CPU), and performs processing of controlling detection light of the light emitter 8, processing of extracting a photoelectric pulse wave signal from the light detection signal, processing of generating pulse wave information based on the photoelectric pulse wave signal, and entire control of the pulse wave sensor device 1.

To be specific, the arithmetic processing unit 17 supplies a control signal for controlling the intensity and timing of the detection light of the light emitter 8 to the light-emitter driver 14, and causes the light emitter 8 to emit the light in accordance with the control signal. Also, the arithmetic processing unit 17 performs processing of extracting the photoelectric pulse wave signal from the light detection signal supplied from the light receiver 9 through the light-detection-signal amplifier 15 and the filter 16. Further, the arithmetic processing unit 17 generates living body information, such as a pulse rate, oxygen saturation, an acceleration pulse wave, and pulse fluctuation, based on the photoelectric pulse wave signal.

The processing circuit 12 may have a configuration in which both the photoelectric-pulse-wave-signal detector 13 and the arithmetic processing unit 17 are mounted on the substrate 10, or a configuration in which only the photoelectric-pulse-wave-signal detector 13 is mounted on the substrate 10. If the photoelectric-pulse-wave-signal detector 13 and the arithmetic processing unit 17 are separated from each other, the arithmetic processing unit 17 may use, for example, a processing device mounted on a game machine etc. for performing processing of the content of a game, or may be provided independently from such a processing device. Also, the arithmetic processing unit 17 may include a memory that stores data of the photoelectric pulse wave signal, and may include a transmitting device that transmits data of the photoelectric pulse wave signal to an external measuring instrument etc.

A blood-flow blockage reducing part 18 is provided at the left side surface 4A of the lever 4 so that, when the palm P contacts the light emitter 8 and the light receiver 9, the blood-flow blockage reducing part 18 contacts a portion of the palm P excluding the center portion M and the wrist-side portion W. A contact portion C of the palm P which contacts the blood-flow blockage reducing part 18 may be, for example, as follows.

When the user grips the lever 4 with the left hand LH, the user tends to strongly grip the lever 4 with the thumb F1 and the other fingers F2 to F5. Hence, the contact portion C of the palm P which contacts the blood-flow blockage reducing part 18 is set, for example, in a portion close to the thumb F1 of the palm P, i.e., in a portion between the index finger F2 and the middle finger F3, and the thumb F1, as a portion in which the contact pressure between the palm P and the lever 4 is likely increased.

Considering the arrangement at the lever 4 with regard to this point, the position of the base of the index finger F2 can be expected with the trigger button 5. Hence, the blood-flow blockage reducing part 18 is arranged at a position in a range from a height being substantially the same as the height of the trigger button 5 to a height lower than the former height by a single finger in the Z direction, and is arranged at a rear portion of the lever 4 with respect to the light emitter 8 and the light receiver 9.

The blood-flow blockage reducing part 18 is formed of a protrusion protruding with respect to the left side surface 4A of the lever 4. The protruding dimension t of the protrusion is set at, for example, a value of 1 mm or larger, and preferably 3 mm or larger. If the protruding dimension t is too small, a pressing force likely acts even on a portion other than the contact portion C of the palm C. In contrast, if the protruding dimension t is too large, a gap is generated between the palm P and the light receiver 9, the distance between the palm P and the light receiver 9 becomes unstable, and hence the measurement value becomes less stable. In addition, since reflection at the interface between the light receiver 9 and the air and the interface between the air and the skin is high, the ratio of light, which is emitted from the light emitter 8, does not enter the skin, and is directly incident on the light receiver 9, is increased. Consequently, the signal to noise ratio (S/N) of the photoelectric pulse wave signal is decreased.

Hence, a specific example of the protruding dimension t is, for example, in a range from about 1 to about 9 mm, and more preferably in a range from about 3 to about 6 mm. Accordingly, a step is formed around the blood-flow blockage reducing part 18.

If the user of the pulse wave sensor device 1 grips the lever 4 with the left hand LH and the measurement portion S of the palm P is arranged at the light emitter 8 and the light receiver 9, the contact portion C between the index finger F2 and the middle finger F3, and the thumb F1 of the palm P, in particular, the portion extending from the bases of the index finger F2 and the middle finger F3 to the base of the thumb F1 contacts the blood-flow blockage reducing part 18. At this time, since the blood-flow blockage reducing part 18 protrudes from the left side surface 4A of the lever 4, the contact portion C between the index finger F2 and the middle finger F3, and the thumb F1 contacts the protruding end surface of the blood-flow blockage reducing part 18 before the other portion of the palm P. Also, the measurement portion S located near the base of the ring finger F4 of the palm P contacts the left side surface 4A of the lever 4. Thus, since the contact portion C of the palm P is supported by the blood-flow blockage reducing part 18 and the measurement portion S is supported by the left side surface 4A of the lever 4, the center portion M and the wrist-side portion W of the palm P different from the contact portion C and the measurement portion S likely have gaps with respect to the lever 4. Consequently, the pressure acting on the center portion M and the wrist-side portion W of the palm P is reduced. Since the compression acting on these portions is reduced, blockage of blood flow in the measurement portion S is restricted.

The blood-flow blockage reducing part 18 may have a mechanism movable in the front-rear direction and/or the up-down direction relative to the lever 4 to adjust the contact portion C of the palm P. Also, the blood-flow blockage reducing part 18 may protrude from the left side surface 4A only when the pulse wave is measured. Further, the blood-flow blockage reducing part 18 may be formed of, for example, a hard metal material or resin material, or may be formed of, for example, a soft material to conform to the palm P.

A distance D1 between the blood-flow blockage reducing part 18 and the light emitter 8 in the Z direction is set based on the size of the palm P and the intervals between the five fingers F1 to F5 of a typical human body. The size of the protruding end surface of the blood-flow blockage reducing part 18 is also set based on a reference similar to the former reference, and has a length of about several tens of millimeters in the Y direction and Z direction.

The pulse wave sensor device 1 according to the first embodiment of the invention has the above-described configuration, and its operation is described next.

First, when the pulse wave sensor device 1 is activated in a state in which the user grips the lever 4 with the left hand LH, the control signal is supplied from the arithmetic processing unit 17 to the light-emitter driver 14, and the light emitter 8 emits the detection light in accordance with the control signal. The detection light is reflected by the palm P of the user, and the reflection light is received by the light receiver 9. Then, the light receiver 9 outputs the light detection signal corresponding to the reflection light. The light detection signal is processed with the current-voltage transformation and then is amplified by the light-detection-signal amplifier 15. The noise of the light detection signal is removed by the filter 16. Then, the light detection signal is supplied to the arithmetic processing unit 17.

The arithmetic processing unit 17 extracts the photoelectric pulse wave signal corresponding to the detection light of the light emitter 8 from the light detection signal supplied from the filter 16. The arithmetic processing unit 17 generates pulse wave information, such as a pulse-wave waveform, a pulse rate, oxygen saturation, and angiosclerosis, based on the extracted photoelectric pulse wave signal.

Figure 6:
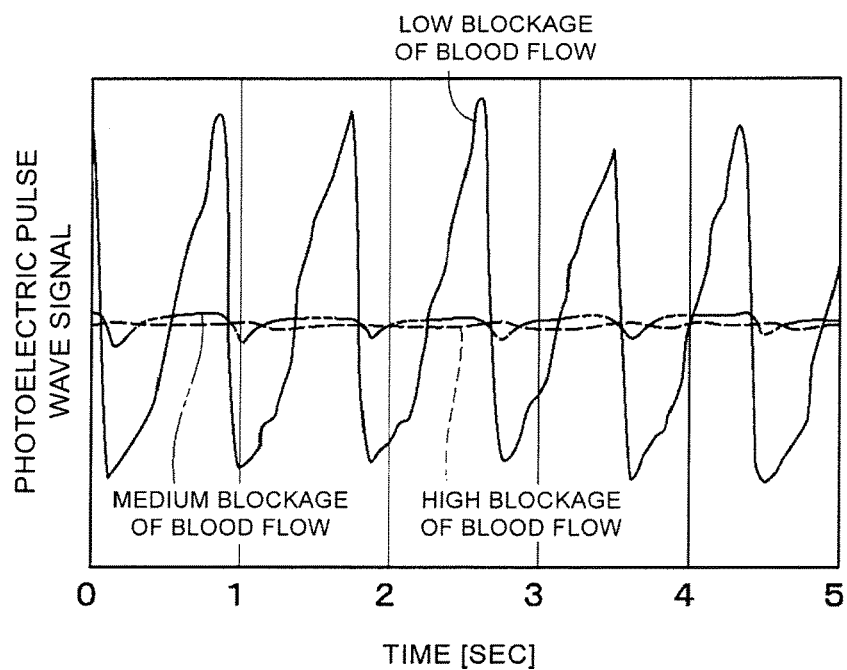
FIG. 6 is a characteristic diagram illustrating a change in photoelectric pulse wave signal over time.

At this time, if the user strongly grips the lever 4, the blood flow of the palm P is blocked, and the pulse wave is no longer detected. If the blood flow is not blocked, a photoelectric pulse wave signal is obtained as indicated by a solid line in FIG. 6. In contrast, if the blood flow is blocked, a variation in photoelectric pulse wave signal becomes small as indicated by a two-dot chain line in FIG. 6, or almost no variation in photoelectric pulse wave signal is provided as indicated by a broken line in FIG. 6. However, the blood flow of the measurement portion S is not always blocked regardless of the portion of the palm P to be pressed. The influence on the blood flow is changed depending on the portion of the palm P to be pressed. That is, the palm P has a portion in which the blood flow is likely blocked, and a portion in which the blood flow is hardly blocked.

Figure 7:
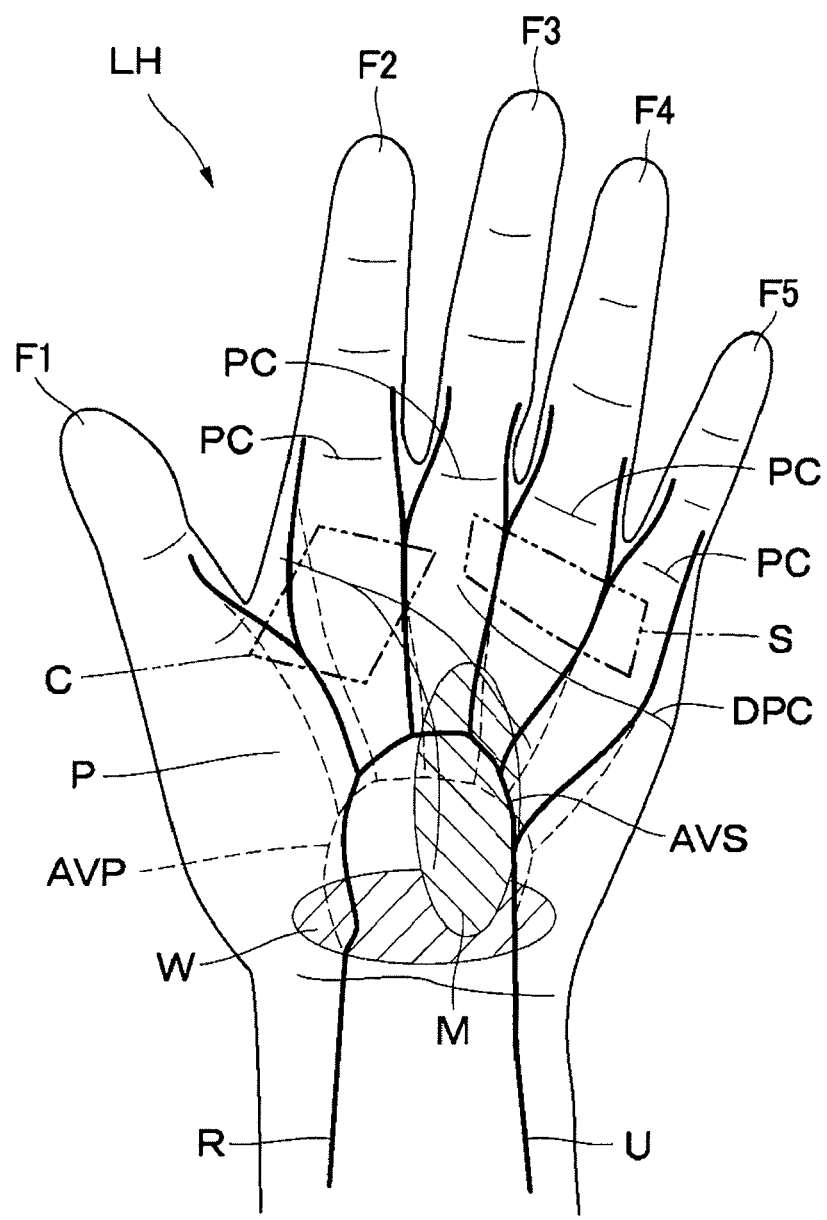
FIG. 7 is an explanatory view illustrating the relationship between a measurement portion by the pulse wave sensor device according to the first embodiment and arteries of the palm.

Hence, the inventor studied this, and found that the blood flow of the palm P is likely blocked when the center portion M or the wrist-side portion W of the palm P is compressed. This point is discussed in detail with reference to FIG. 7.

A hand of a human body (for example, the left hand LH) is supplied with blood mainly through a radial artery R and an ulnar artery U of an arm and arteries branched from these arteries R and U. These arteries are combined in the palm P and form double arches of a superficial palmar arterial arch AVS and a deep palmer arterial arch AVP, and arteries to the five fingers F1 to F5 are branched from the double arches. The superficial palmar arterial arch AVS and the deep palmar arterial arch AVP are formed at the center portion M of the palm P. Hence, if the center portion M of the palm P is compressed, it is conceived that the superficial palmar arterial arch AVS etc. is flattened and the blood flow of the palm P is generally blocked. Also, even when the wrist-side portion W is compressed, this may likely influence the radial artery R and the ulnar artery U, and the blood flow of the palm P tends to be blocked.

With regard to this point, in this embodiment, the measurement portion S is set at the portion excluding the center portion M and the wrist-side portion W of the palm P, as a portion in which the pulse wave is easily measured. To be specific, the measurement portion S is set near the bases of the middle finger F3, the ring finger F4, and the little finger F5 of the palm P, as the position in which the pulse wave can be stably detected even when the lever 4 is operated. In addition, the blood-flow blockage reducing part 18 protruding from the left side surface 4A of the lever 4 is brought into contact with the portion excluding the center portion M and the wrist-side portion W of the palm P, more specifically, the portion between the index finger F2 and the middle finger F3, and the thumb F1, as the contact portion C.

When the user arranges the measurement portion S of the palm P at the light emitter 8 and the light receiver 9, the contact portion C, which is different from the center portion M and the wrist-side portion W, of the palm P contacts the blood-flow blockage reducing part 18. Accordingly, the pressing force acting on the center portion M and the wrist-side portion W can be reduced. Consequently, as compared with the measurement portion S of the palm P, the compression acting on the center portion M and the wrist-side portion W is reduced, and the blockage of the blood flow in the entire palm P including the measurement portion S can be reduced.

As described above, with the pulse wave sensor device 1 according to the first embodiment, the light emitter 8 and the light receiver 9 are arranged at the positions so as to face the palm P and the pulse wave of the palm P is detected. Owing to this, even when the fingers F1 to F5 move, the blood flow of the palm P located at the upstream side can become relatively stable. As compared with that the pulse wave is detected at a fingertip, the pulse wave can be stably detected.

Also, the light emitter 8 and the light receiver 9 are arranged at the portion excluding the center portion M and the wrist-side portion W of the palm P, and the blood-flow blockage reducing part 18 contacts that portion. In this case, since a step is formed around the blood-flow blockage reducing part 18, the compression acting on a portion at the upstream side of blood flow with respect to the measurement portion S of the palm P can be reduced. The portion at the upstream side is the center portion or the wrist-side portion of the palm, for example. Consequently, even if the palm P is strongly pressed to the light emitter 8 and the light receiver 9, the blood flow is not blocked at the measurement portion S, the burden of the user is reduced, and the pulse wave can be easily detected.

Also, the measurement portion S is set at the portion close to the bases of the fingers F3 to F5 with respect to the center portion M of the palm P. To be specific, since the measurement portion S is set near the base of the ring finger F4, when the user grips the lever 4 with the left hand LH, the peripheral portion of the element openings 6A and 6B of the lever 4 contacts the palm P, and the light emitter 8 and the light receiver 9 can easily approach the measurement portion S.

In addition, when the lever 4 is gripped with the left hand LH, the blood-flow blockage reducing part 18 contacts the portion between the index finger F2 and the middle finger F3, and the thumb F1 of the palm P. Accordingly, even when the user strongly grips the lever 4, the step is formed around the blood-flow blockage reducing part 18, the compression on the center portion M and the wrist-side portion W of the palm P is reduced, the blood-flow blockage can be restricted, and the pulse wave can be stably detected. Also, since the measurement portion S is the portion close to the bases of the fingers F3 to F5 with respect to the center portion M of the palm P, even when the fingertips move by the operation of the lever 4 or the pressing operation of the trigger button 5, the influence on the blood flow in the measurement portion S can be reduced. Accordingly, even when the lever 4 is operated, the pulse wave can be stably detected.

Figure 8:
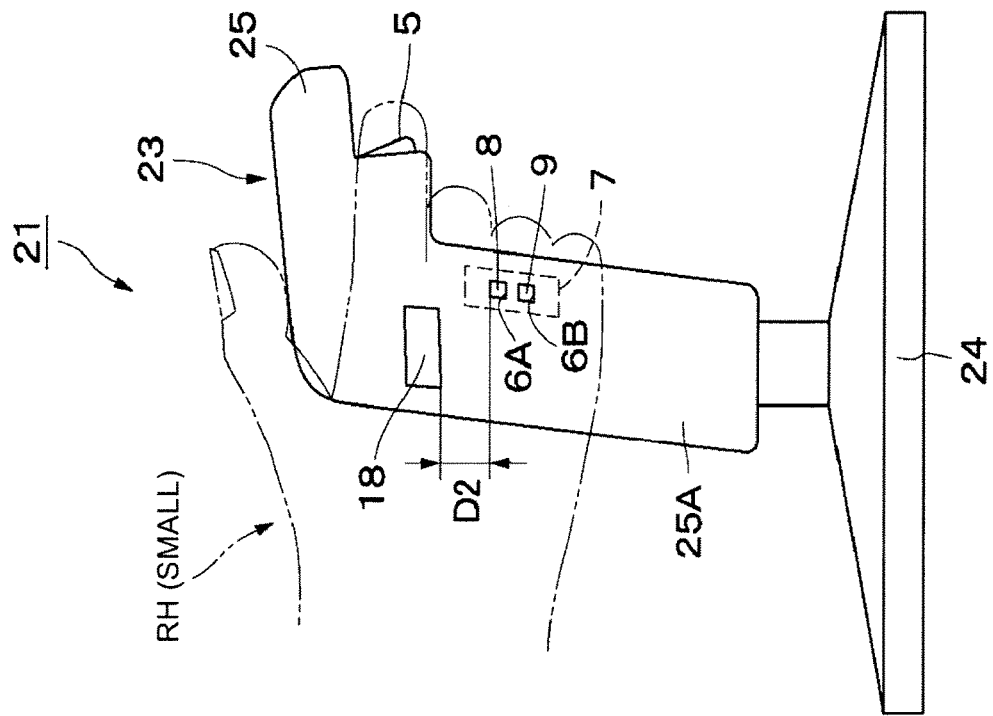
FIG. 8 is a front view illustrating a pulse wave sensor device according to a second embodiment.
Figure 8:
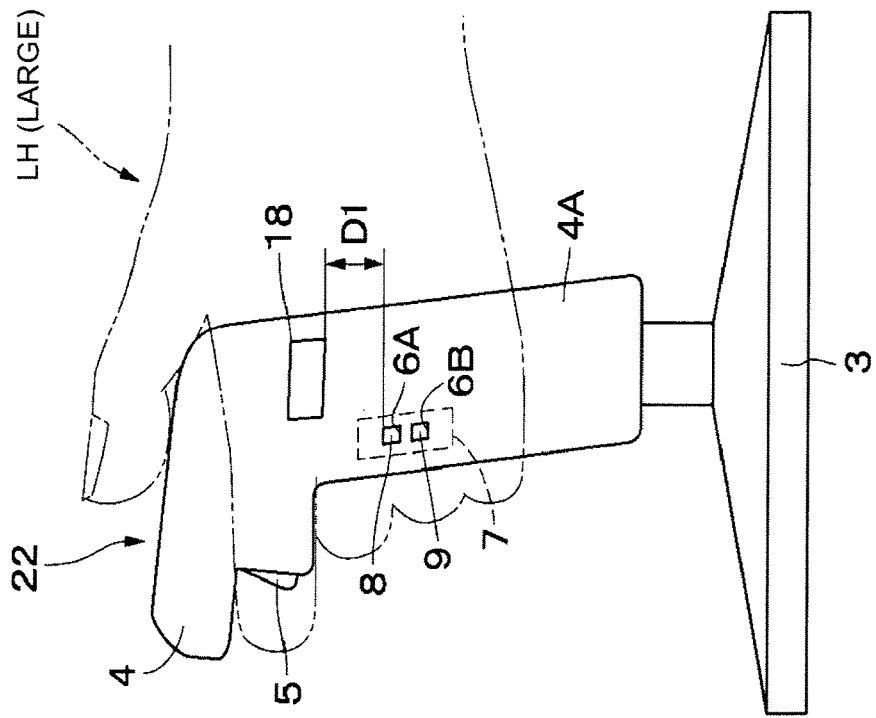

Next, FIG. 8 illustrates a second embodiment of the invention. A feature of this embodiment is a configuration in which the positions of a light emitter and a light receiver attached to a right-hand lever differ from the positions of a light emitter and a light receiver attached to a left-hand lever. In this embodiment, the same reference sign is applied to the same component of the first embodiment, and the description is omitted.

A pulse wave sensor device 21 has a configuration, in which a sensor unit 7 and a blood-flow blockage reducing part 18 are attached to each of a left-hand lever device 22 and a right-hand lever device 23, substantially similarly to the pulse wave sensor device 1 according to the first embodiment.

The left-hand lever device 22 includes a pedestal 3, a lever 4 serving as a sensor attachment body, and a trigger button 5 at the front side of the lever 4, similarly to the lever device 2 according to the first embodiment. The right-hand lever device 23 also includes a pedestal 24, a lever 25 serving as a sensor attachment body, and a trigger button 5 at the front side of the lever 25, substantially similarly to the left-hand lever device 22. The right-hand lever 25 has a shape that is left-right symmetric to the shape of the left-hand lever 4.

The left-hand lever device 22 has the sensor unit 7 and the blood-flow blockage reducing part 18 at a left side surface 4A of the lever 4. In contrast, the right-hand lever device 23 has the sensor unit 7 and the blood-flow blockage reducing part 18 at a right side surface 25A of the lever 25.

Also, in the left-hand lever device 22, a distance D1 between the blood-flow blockage reducing part 18 and the light emitter 8 in the Z direction is set on the basis of the size of the palm P of the left hand LH of a typical adult. In contrast, in the right-hand lever device 23, a distance D2 between the blood-flow blockage reducing part 18 and the light emitter 8 in the Z direction is set on the basis of the size of the palm P of the right hand RH of a typical child (for example, in a range from about 6 to about 12 years old).

Owing to this, the value of the distance D2 at the right-hand side is smaller than the value of the distance D1 at the left-hand side. Hence, the attachment position of the light emitter 8 at the left-hand lever device 22 differs from the attachment position of the light emitter 8 at the right-hand lever device 23. Owing to this, the attachment position of the light receiver 9 arranged around the light emitter 8 at the left-hand lever device 22 differs from the attachment position of the light receiver 9 arranged around the light emitter 8 at the right-hand lever device 23.

Thus, even with the second embodiment, effects and advantages similar to those of the first embodiment can be obtained. In particular, in the second embodiment, the light emitter 8 and the light receiver 9 are attached at the left-hand lever 4 at the positions different from the positions at the right-hand lever 25. Accordingly, even if the size of the palm P varies depending on the user of the pulse wave sensor device 21, for example, in a case of an adult and a child, the light emitter 8 and the light receiver 9 can be brought into contact with the proper measurement portion of the palm P by using at least one of the left-hand lever 4 and the right-hand lever 25, and hence the difference in size of the palm P depending on the user can be allowed. Consequently, for example, photoelectric pulse wave signals output from the left-hand and right-hand lever devices 22 and 23 may be compared with each other, correct one of the signals may be selected, and the stability of measurement can be increased.

In the second embodiment, while the attachment positions of the light emitter 8 and the light receiver 9 at the left-hand lever 4 differ from those at the right-hand lever 25, in addition, the size and protruding dimension of the blood-flow blockage reducing part 18 of the left-hand lever 4 may differ from those of the right-hand lever 25.

Also, while the left-hand lever device 22 and the right-hand lever device 23 use the different pedestals 3 and 24, two left-hand and right-hand levers may be attached to a single pedestal.

Figure 9:
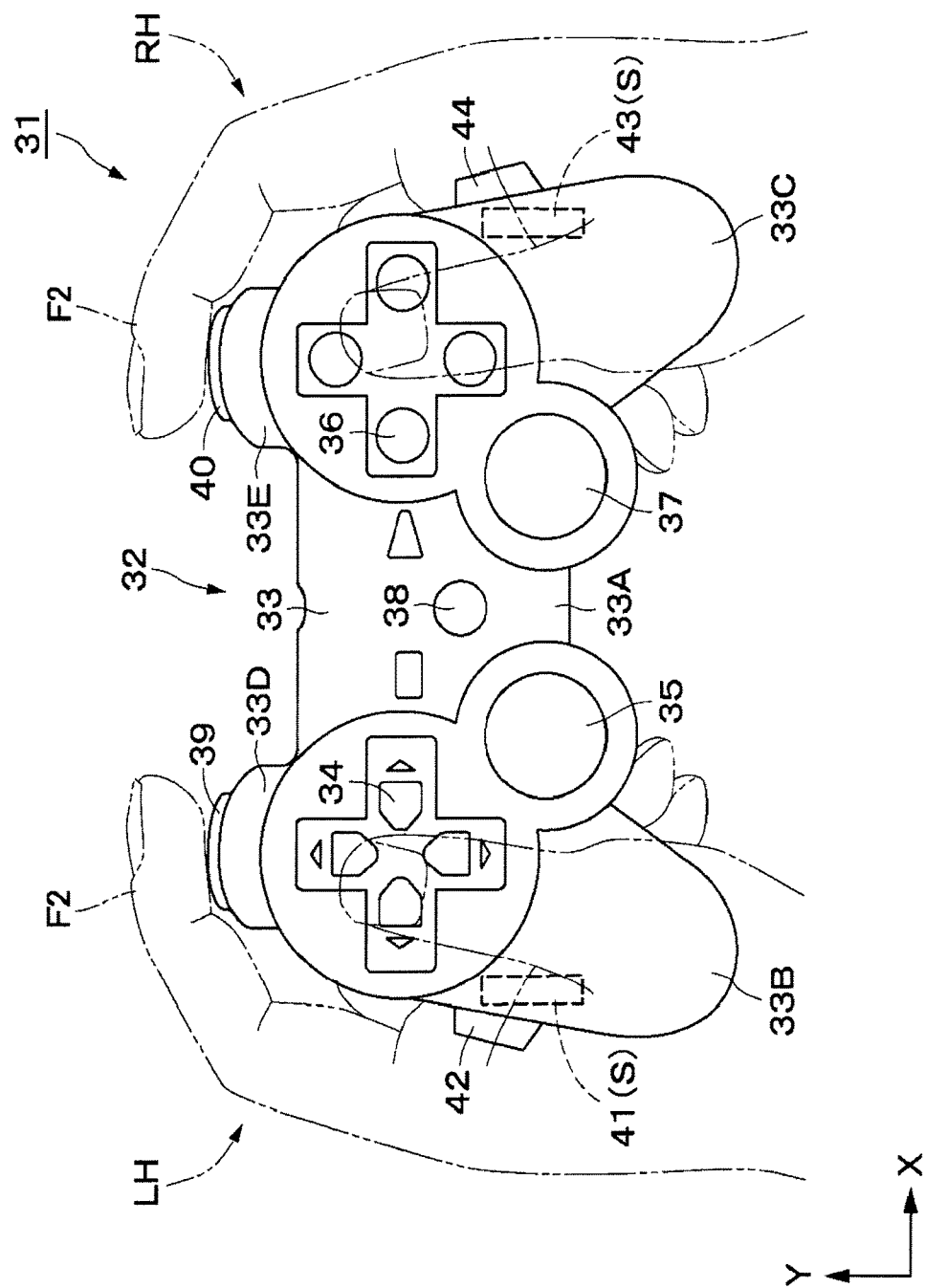
FIG. 9 is a plan view illustrating a pulse wave sensor device according to a third embodiment.
Figure 10:
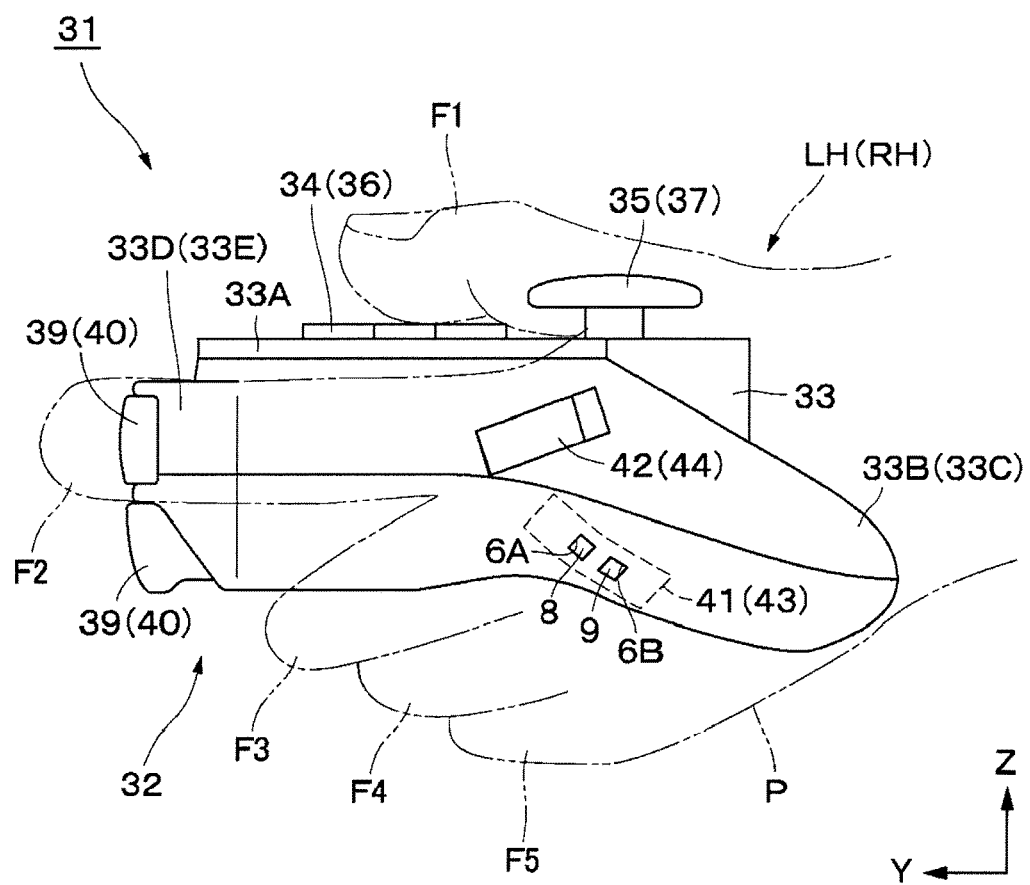
FIG. 10 is a side view from the left side of the pulse wave sensor device in FIG. 9.

Next, FIGS. 9 and 10 illustrate a third embodiment of the invention. A feature of this embodiment is a configuration in which a light emitter and a light receiver are attached to a game controller that is operated by fingertips while being gripped with hands. In this embodiment, the same reference sign is applied to the same component of the first embodiment, and the description is omitted.

A pulse wave sensor device 31 is applied to, for example, a game controller 32 serving as an operation device that operates an operation subject in a game screen.

The game controller 32 is held with both hands (left hand LH and right hand RH) of a user, and includes a casing 33 that forms a sensor attachment body. The casing 33 includes a body part 33A having a box-like shape and extending in the left-right direction (Y direction), left and right grip parts 33B and 33C provided at both ends in the Y direction of the body part 33A, and left and right forward protruding parts 33D and 33E protruding forward from the body part 33A.

A plurality of buttons 34 for operation with the thumb F1 of the left hand LH are provided at a left portion of the upper surface of the body part 33A. Also, a stick-type analog input part 35 is provided at the near side (rear side) of the buttons 34. Similarly, a plurality of buttons 36 and an analog input part 37 for operation with the thumb F1 of the right hand RH are provided at a right portion of the upper surface of the body part 33A. Further, a plurality of buttons 38 for performing, for example, mode change, are provided at a center portion of the upper surface of the body part 33A.

Also, two buttons 39 for operation with the index finger F2 of the left hand LH are provided at the forward protruding part 33D at the left side. These buttons 39 are separated in the up-down direction, and protrude forward. Similarly, two buttons 40 for operation with the index finger F2 of the right hand RH are provided at the forward protruding part 33E at the right side.

The casing 33 has a signal output circuit (not illustrated) therein. The signal output circuit outputs signals from the buttons 34, 36, 38, 39, and 40 and signals from the analog input parts 35 and 37. The game controller 32 is connected with, for example, a game machine or a computer by a wired method or a wireless method, and outputs a signal from the signal output circuit to the game machine etc., similarly to the lever device 2 according to the first embodiment.

The left grip part 33B has a substantially triangular shape and extends from the left side of the body part 33A obliquely rearward. The grip part 33B has a substantially elliptic cross section, and is gripped with the thumb F1 and the thenar, which is a base portion of the thumb F1, as well as the middle finger F3, the ring finger F4, and the little finger F5 of the left hand LH.

A sensor unit 41, which is substantially similar to the sensor unit 7 according to the first embodiment, is attached to the left side surface of the grip part 33B. The sensor unit 41 includes a light emitter 8 and a light receiver 9. The light emitter 8 and the light receiver 9 are arranged at positions close to the bottom surface of the grip part 33B, and are inserted into element openings 6A and 6B provided at the grip part 33B. Accordingly, when the user grips the grip part 33B with the left hand LH, the light emitter 8 and the light receiver 9 are arranged at, for example, a portion close to the bases of the middle finger F3, the ring finger F4, and the little finger F5, as a measurement portion S of the palm P of the left hand LH.

Also, a blood-flow blockage reducing part 42 protruding leftward is provided at the left side surface of the grip part 33B. The blood-flow blockage reducing part 42 is formed substantially similarly to the blood-flow blockage reducing part 18 according to the first embodiment, and is arranged above the light emitter 8 and the light receiver 9. Hence, when the user grips the game controller 32 with the left hand LH, the blood-flow blockage reducing part 42 contacts, for example, a portion between the index finger F2 and the middle finger F3, and the thumb F1, as a contact portion C of the palm P of the left hand LH.

Similarly, the right grip part 33C has a substantially triangular shape and extends from the right side of the body part 33A obliquely rearward. The right grip part 33C is gripped with the thumb F1 and the thenar, which is a base portion of the thumb F1, as well as the middle finger F3, the ring finger F4, and the little finger F5 of the right hand RH.

A sensor unit 43 and a blood-flow blockage reducing part 44 are provided at the right side surface of the grip part 33C, at positions left-right symmetric to the positions of the sensor unit 41 and the blood-flow blockage reducing part 42. Accordingly, when the user grips the grip part 33C with the right hand RH, a light emitter 8 and a light receiver 9 of the sensor unit 43 are arranged at, for example, a portion close to the bases of the middle finger F3, the ring finger F4, and the little finger F5, as a measurement portion S of the palm P of the right hand RH. At this time, the blood-flow blockage reducing part 44 provided at the right side surface of the grip part 33C contacts, for example, a portion between the index finger F2 and the middle finger F3, and the thumb F1, as a contact portion C of the palm P of the right hand RH.

Thus, even with the third embodiment, effects and advantages similar to those of the first embodiment can be obtained. Also, since the light emitter 8 and the light receiver 9 are provided at the grip part 33B, 33C of the game controller 32, the pulse wave can be detected while a portion around the light emitter 8 and the light receiver 9 of the grip part 33B, 33C contacts the palm P and the light emitter 8 and the light receiver 9 are arranged at the measurement portion S of the palm P of the user. Thus, even when the game controller 32 is operated with fingertips, the influence on blood flow in the measurement portion S can be reduced, and the pulse wave can be stably detected.

In the third embodiment, the light emitter 8 and the light receiver 9 at the left grip part 33B and the light emitter 8 and the light receiver 9 at the right grip part 33C are arranged at the left-right symmetric positions. However, the invention is not limited thereto, and like the second embodiment, the light emitter 8 and the light receiver 9 at the left grip part 33B may be arranged at positions different from the positions of the light emitter 8 and the light receiver 9 at the right grip part 33C. Also, the light emitter 8 and the light receiver 9 may be attached to only one of the left and right grip parts 33B and 33C.

Further, in the third embodiment, the game controller 32 held with both hands is exemplified. However, the configuration may be applied to a game controller held with one hand.

Figure 11:
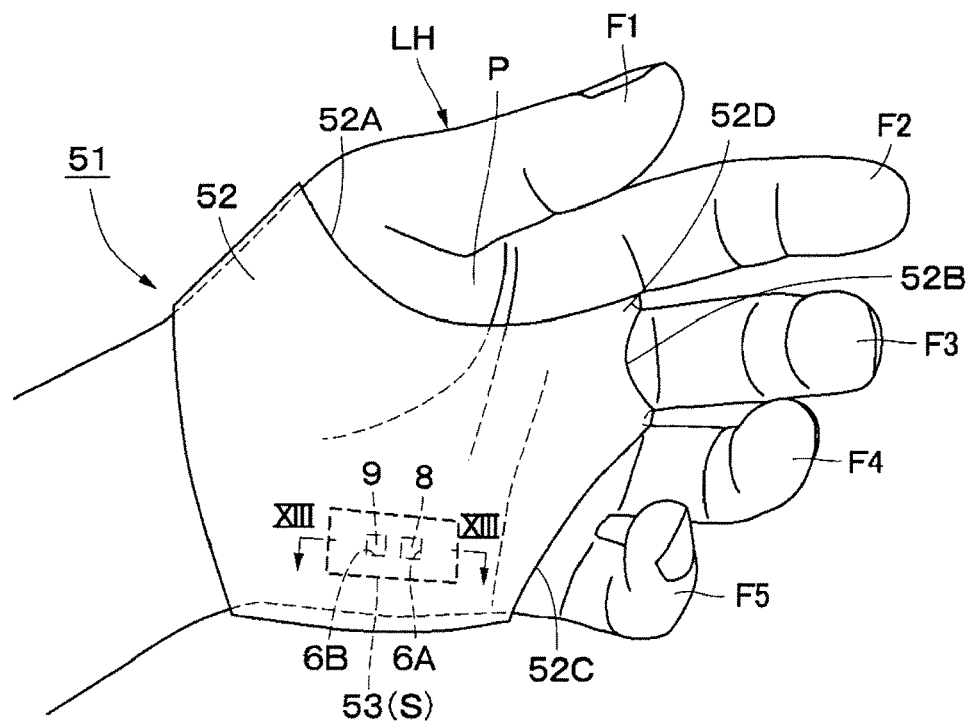
FIG. 11 is a perspective view illustrating a state in which a user wears a pulse wave sensor device according to a fourth embodiment on the left hand.
Figure 12:
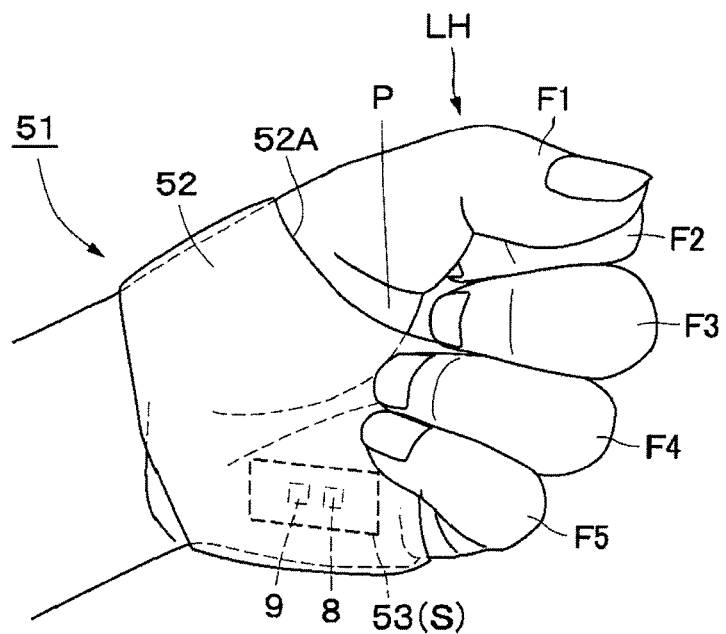
FIG. 12 is a perspective view illustrating a state in which the user wears the pulse wave sensor device in FIG. 11 and closes the left hand.
Figure 13:
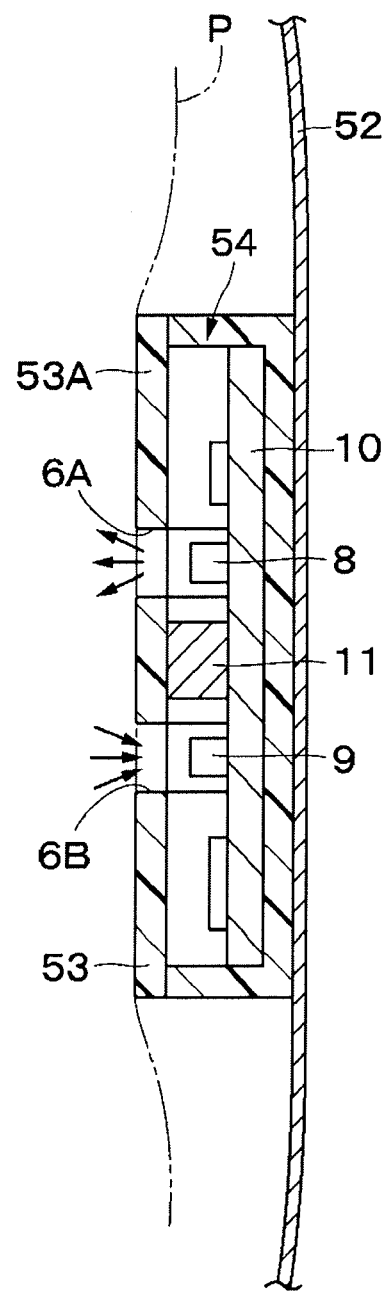
FIG. 13 is a cross-sectional view of a light emitter, a light receiver, and other part of the pulse wave sensor device taken along arrow XIII-XIII in FIG. 11.

Next, FIGS. 11 to 13 illustrate a fourth embodiment of the invention. A feature of this embodiment is a configuration in which a sensor casing is attached to a fixing tool that is worn on a palm, and a light emitter and a light receiver housed in the sensor casing are arranged at the hypothenar of the palm. In this embodiment, the same reference sign is applied to the same component of the first embodiment, and the description is omitted.

A pulse wave sensor device 51 includes a fixing tool 52 and a sensor casing 53. The fixing tool 52 is formed in a substantially bag-like or cylinder-like shape, by using a bandage or an expansion cloth. The fixing tool 52 has three finger through holes 52A to 52C. The thumb F1 and the index finger F2 are inserted into the finger through hole 52A, the middle finger F3 is inserted into the finger through hole 52B, and the ring finger F4 and the little finger F5 are inserted into the finger through hole 52C. Hence, when the fixing tool 52 is worn on the palm P while the fingers F1 to F5 are inserted into the corresponding finger through holes 52A to 52C, a ring-shaped finger hook part 52D surrounding the finger through hole 52B is hooked at the periphery of the base of the middle finger F3.

The sensor casing 53 is attached to the inside of the fixing tool 52. The sensor casing 53 is formed in, for example, a substantially rectangular box-like shape, and protrudes to the palm P with respect to the fixing tool 52. Also, a protruding end surface 53A of the sensor casing 53 serves as a contact surface with the palm P, and has two element openings 6A and 6B.

A sensor unit 54, which is similar to the sensor unit 7 according to the first embodiment, is mounted in the sensor casing 53. To be specific, as illustrated in FIG. 13, a substrate 10 with a light emitter 8 and a light receiver 9 mounted is housed in the sensor casing 53, and the light emitter 8 and the light receiver 9 are arranged at positions so as to face the element openings 6A and 6B, respectively.

The sensor casing 53 is arranged at a position corresponding to the hypothenar HE of the palm P. Hence, the light emitter 8 and the light receiver 9 are arranged at the hypothenar HE of the palm P, as a measurement portion S excluding a center portion M and a wrist-side portion W of the palm P. Also, since the sensor casing 53 protrudes to the palm P with respect to the fixing tool 52, a step is formed around the sensor casing 53. Accordingly, the sensor casing 53 functions as a blood-flow blockage reducing part, and reduces compression acting on the center portion M and the wrist-side portion W of the palm P.

Figure 14:
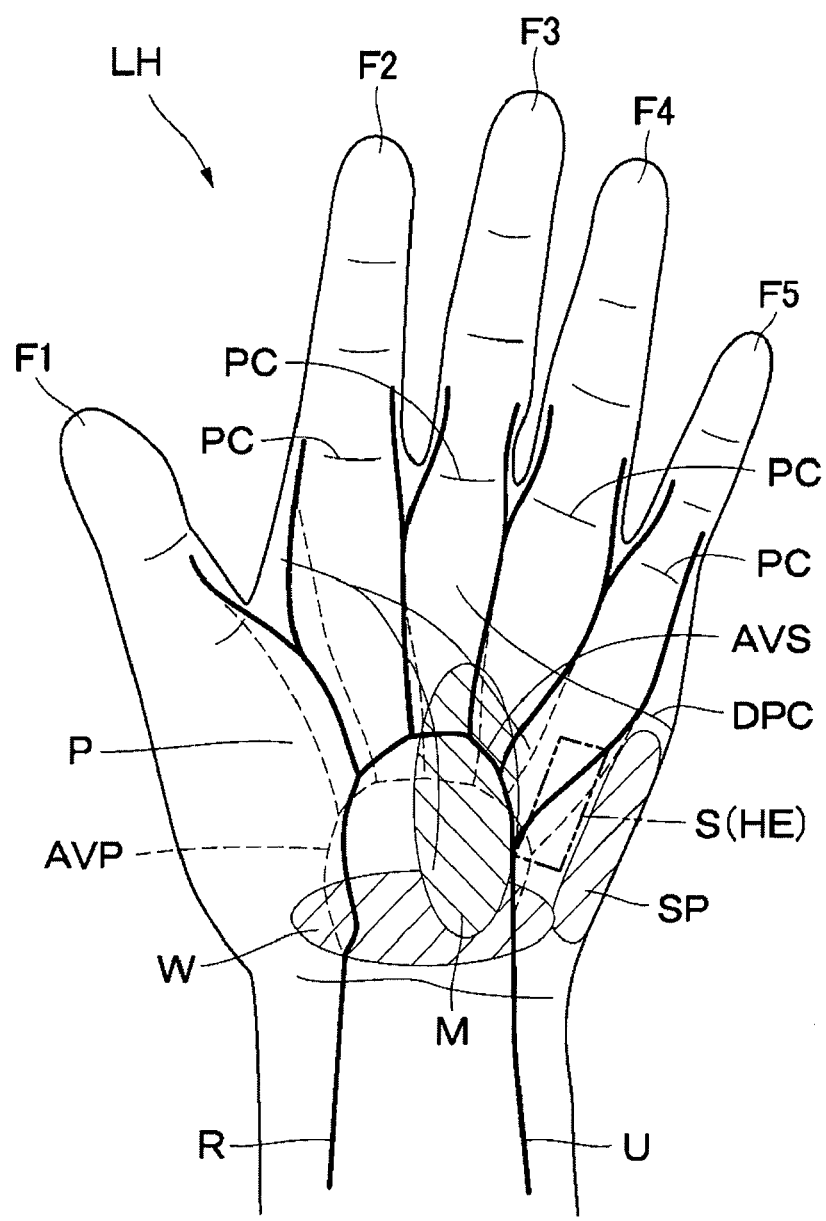
FIG. 14 is an explanatory view illustrating the relationship between a measurement portion of the pulse wave sensor device according to the fourth embodiment and arteries of the palm.

Thus, even with the fourth embodiment, effects and advantages similar to those of the first embodiment can be obtained. As illustrated in FIG. 14, in the fourth embodiment, the measurement portion S is the hypothenar HE of the palm P. In this case, since the hypothenar HE of the palm P is softer than the other portion, even when the sensor casing 53 housing the light emitter 8 and the light receiver 9 is brought into strong contact with the hypothenar HE of the palm P, the blood flow is less likely blocked. Accordingly, the pulse wave can be detected even when the sensor casing 53 is strongly pressed to the measurement portion S of the palm P, and the pulse wave can be measured even more stably when the sensor casing 53 is strongly pressed.

In addition, as illustrated in FIG. 12, even when the left hand LH is closed, a fingertip hardly contacts the hypothenar HE of the palm P. The sensor casing 53 less likely becomes an obstruction although the sensor casing 53 is attached in contact with the hypothenar HE. Accordingly, by using the light emitter 8 and the light receiver 9 provided in the sensor casing 53, the pulse wave can be detected, for example, even during physical activity.

The pulse wave during physical activity can be detected at the wrist; however, S/N of the photoelectric pulse wave signal may become unstable. The reason is considered as follows. For example, in the case of the wrist, the position at which the pulse wave can be detected is limited. If the wrist is turned, the photoelectric pulse wave signal is no longer obtained. The size of the wrist and the position of arteries may vary depending on an individual. In contrast, if the pulse wave is measured at the palm P like the fourth embodiment, such problems less likely occur, and S/N of the photoelectric pulse wave signal even during physical activity can become stable.

When the pulse wave is detected at the hypothenar HE, the blood flow is likely blocked even when a side surface portion SP close to the little finger F5 of the palm P is strongly compressed, in addition to the case of the center portion M and the wrist-side portion W of the palm P (see FIG. 14). Hence, a portion of the fixing tool 52, the portion which is brought into contact with the side surface portion SP, may use a softer material than the material of the other portion, or a cushion may be provided. Also, a hole may be provided in the fixing tool 52 at a position so as to face the side surface portion SP.

Figure 15:
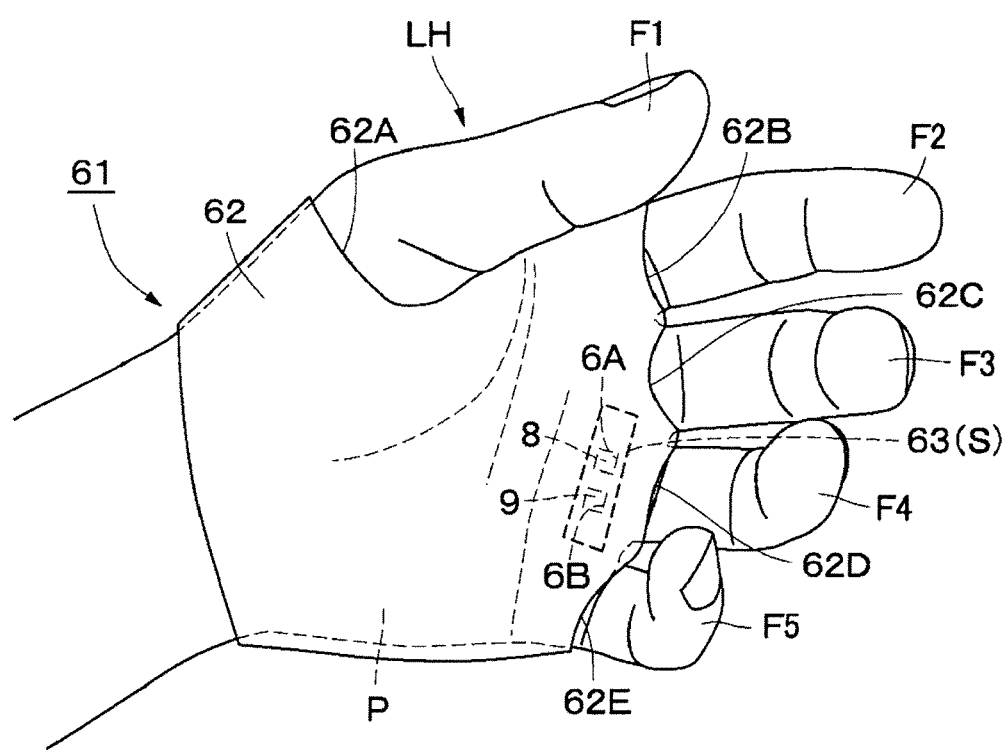
FIG. 15 is a perspective view illustrating a state in which a user wears a pulse wave sensor device according to a fifth embodiment on the left hand.
Figure 16:
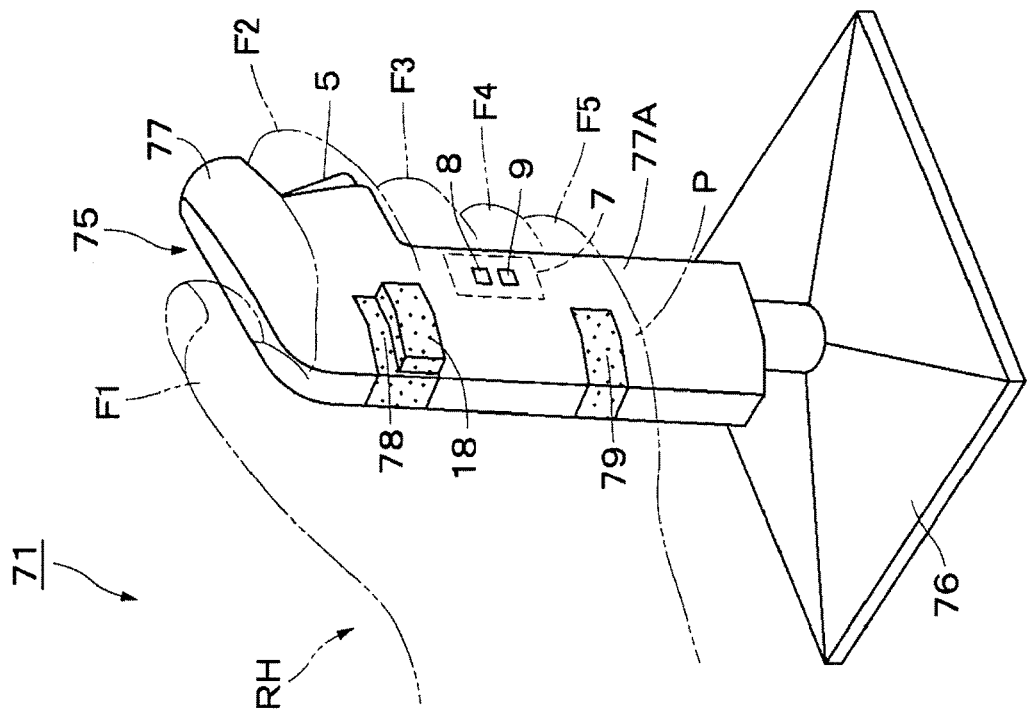
FIG. 16 is a perspective view illustrating a pulse wave sensor device according to a sixth embodiment.
Figure 16:
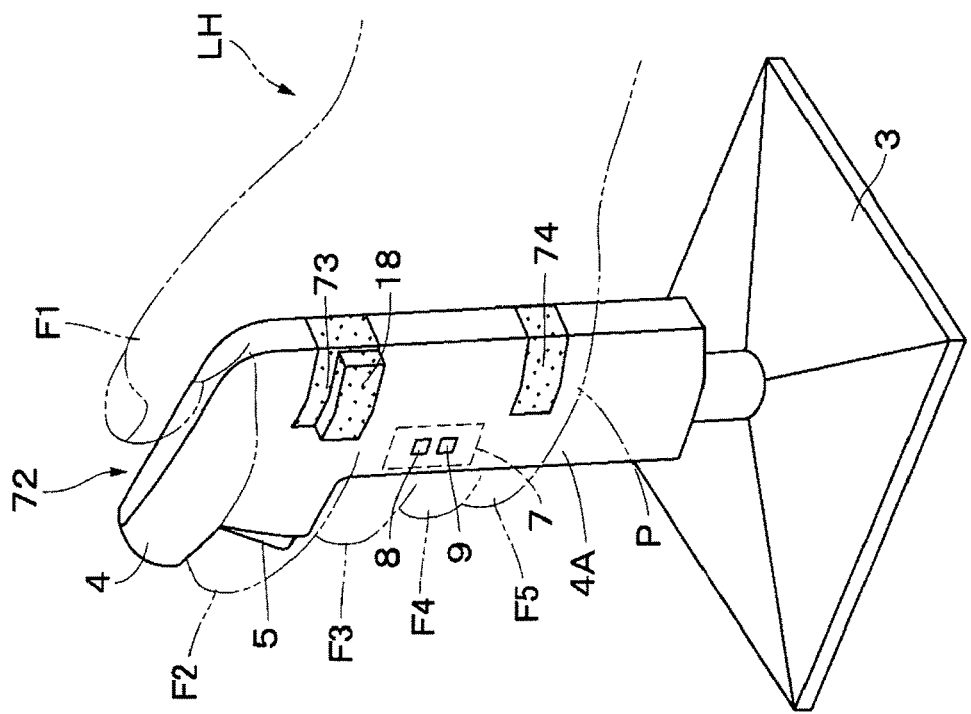
Figure 17:
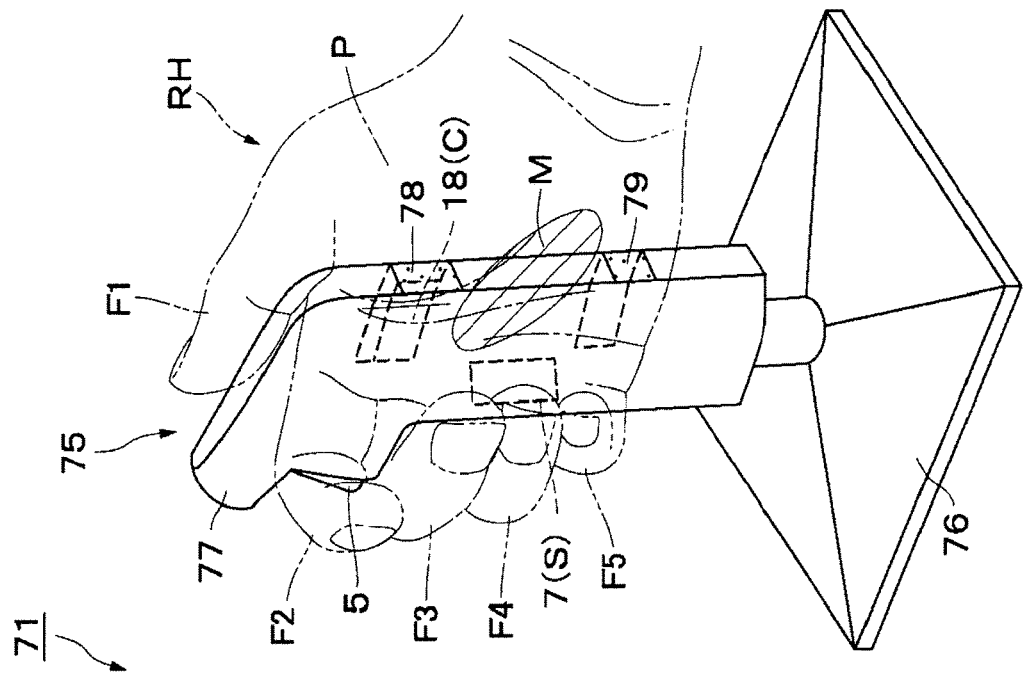
FIG. 17 is a perspective view of the pulse wave sensor device according to the sixth embodiment in a direction different from FIG. 16.
Figure 17:
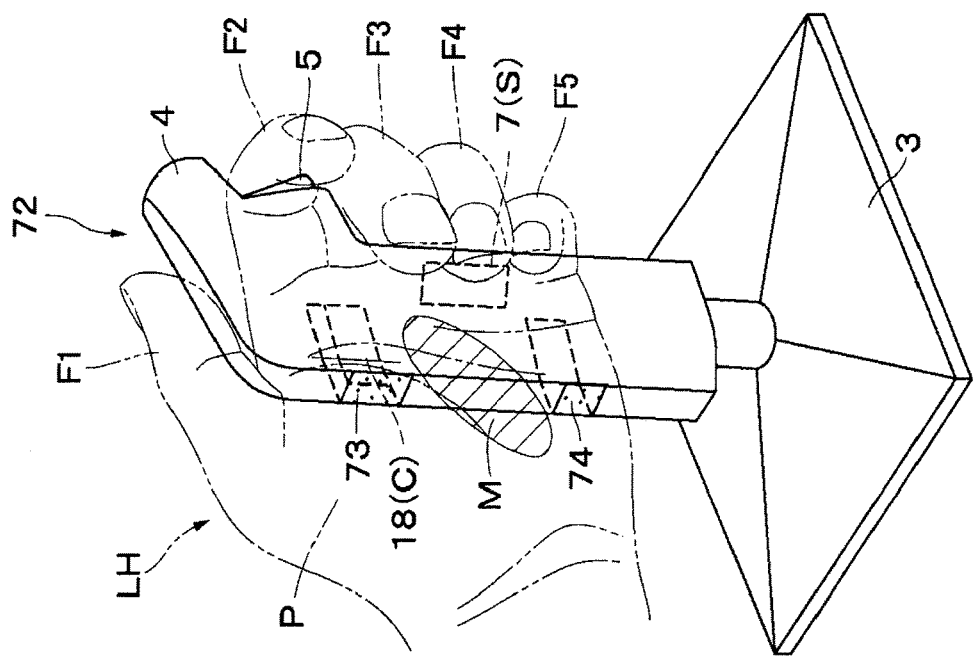

Next, FIG. 15 illustrates a fifth embodiment of the invention. A feature of this embodiment is a configuration in which a sensor casing is attached to a fixing tool that is worn on a palm, and a light emitter and a light receiver housed in the sensor casing are arranged at a portion close to the base of the ring finger of the palm. In this embodiment, the same reference sign is applied to the same component of the first embodiment, and the description is omitted.

A pulse wave sensor device 61 includes a fixing tool 62 and a sensor casing 63. The fixing tool 62 has five finger through holes 62A to 62E corresponding to the five fingers F1 to F5, respectively, and is formed in a glove-like shape without portions for the fingers F1 to F5.

The sensor casing 63 is attached to the inside of the fixing tool 62. The sensor casing 63 is formed substantially similarly to the sensor casing 53 according to the fourth embodiment. The sensor casing 63 protrudes to the palm P with respect to the fixing tool 62, and has two element openings 6A and 6B at a protruding end surface of the sensor casing 63. A sensor unit (not illustrated) similar to the sensor unit 7 according to the first embodiment is mounted in the sensor casing 63. Also, a light emitter 8 and a light receiver 9 are arranged at positions so as to face the element openings 6A and 6B, respectively.

The sensor casing 63 is arranged at a position corresponding to a position close to the base of the ring finger F4 of the palm P. Hence, the light emitter 8 and the light receiver 9 are arranged near the base of the ring finger F4 of the palm P, as a measurement portion S excluding a center portion M and a wrist-side portion W of the palm P. Also, since the sensor casing 63 protrudes to the palm P with respect to the fixing tool 62, a step is formed around the sensor casing 63. Accordingly, the sensor casing 63 functions as a blood-flow blockage reducing part, and reduces compression acting on the center portion M and the wrist-side portion W of the palm P.

Thus, even with the fifth embodiment, effects and advantages similar to those of the first embodiment can be obtained.

Next, FIGS. 16 to 19 illustrate a sixth embodiment of the invention. A feature of this embodiment is that an electrocardiograph electrode is provided at the surface position of a blood-flow blockage reducing part. In this embodiment, the same reference sign is applied to the same component of the first embodiment, and the description is omitted.

A pulse wave sensor device 71 has a configuration, in which a sensor unit 7 and a blood-flow blockage reducing part 18 are attached to each of a left-hand lever device 72 and a right-hand lever device 75, substantially similarly to the pulse wave sensor device 1 according to the first embodiment.

The left-hand lever device 72 includes a pedestal 3, a lever 4 serving as a sensor attachment body, and a trigger button 5 at the front side of the lever 4, similarly to the lever device 2 according to the first embodiment. The left-hand lever device 72 has the sensor unit 7 and the blood-flow blockage reducing part 18 at a left side surface 4A of the lever 4. The blood-flow blockage reducing part 18 is formed of a protrusion protruding with respect to the left side surface 4A of the lever 4, and contacts, for example, a portion close to the thumb F1 of the palm P, that is, a portion between the index finger F2 and the middle finger F3, and the thumb F1 of the palm P.

The left-hand lever device 72 is provided with an electrocardiograph electrode 73 for measuring an electrocardiograph signal, at the surface position and the peripheral position of the blood-flow blockage reducing part 18. The electrocardiograph electrode 73 entirely covers, for example, the protruding end surface and the side surfaces of the blood-flow blockage reducing part 18, and covers a position of the left side surface 4A of the lever 4 at the upper side of the blood-flow blockage reducing part 18 and a position of the lever 4 at the rear side of the blood-flow blockage reducing part 18. Accordingly, when the user grips the lever 4 with the left hand LH, the electrocardiograph electrode 73 stably contacts the palm P of the left hand LH of the user.

Also, the left-hand lever device 72 is provided with a ground electrode 74 in a lower portion of the lever 4, at a position close to the pedestal 3 with respect to the sensor unit 7. The ground electrode 74 is arranged at a position different from the position of the electrocardiograph electrode 73, by a distance of, for example, 10 mm or larger. To be specific, the ground electrode 74 is attached at a position of the lever 4 so as to contact the hypothenar of the palm P. The ground electrode 74 is connected with a ground potential.

The right-hand lever device 75 also includes a pedestal 76, a lever 77 serving as a sensor attachment body, and a trigger button 5 at the front side of the lever 77, substantially similarly to the left-hand lever device 72. The right-hand lever 77 has a shape that is left-right symmetric to the shape of the left-hand lever 4. The right-hand lever device 75 has the sensor unit 7 and the blood-flow blockage reducing part 18 at a right side surface 77A of the lever 77. Also, the right-hand lever device 75 is provided with an electrocardiograph electrode 78 and a ground electrode 79, substantially similarly to the left-hand lever device 72.

Figure 18:
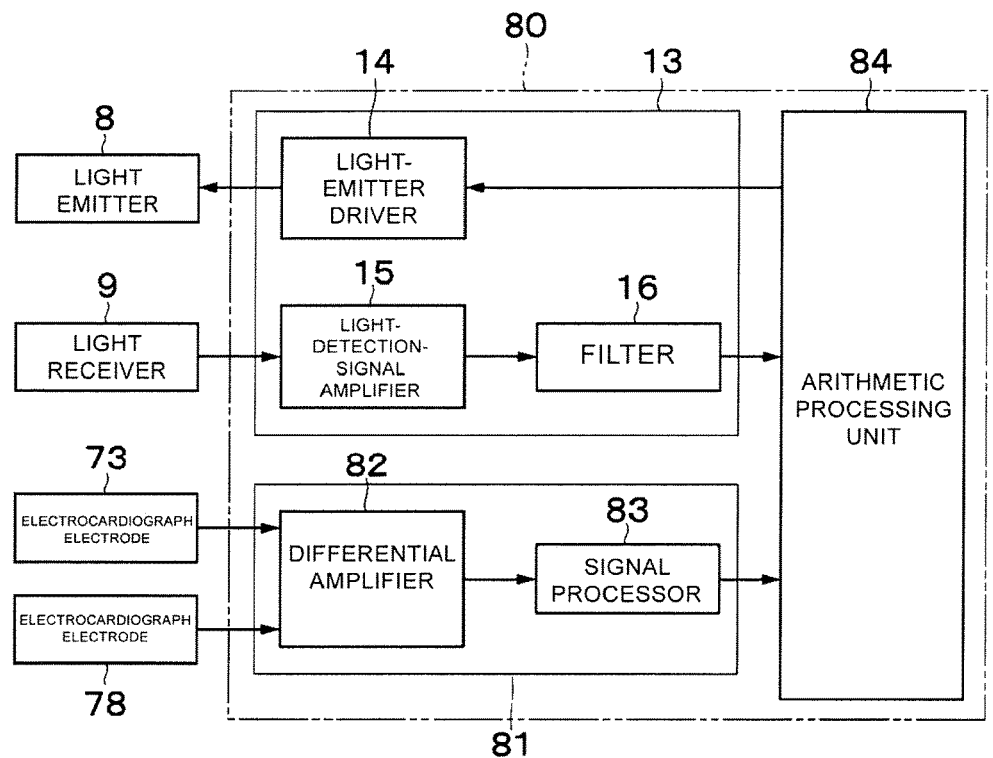
FIG. 18 is a block diagram illustrating an electric configuration of the pulse wave sensor device according to the sixth embodiment.
Figure 19:
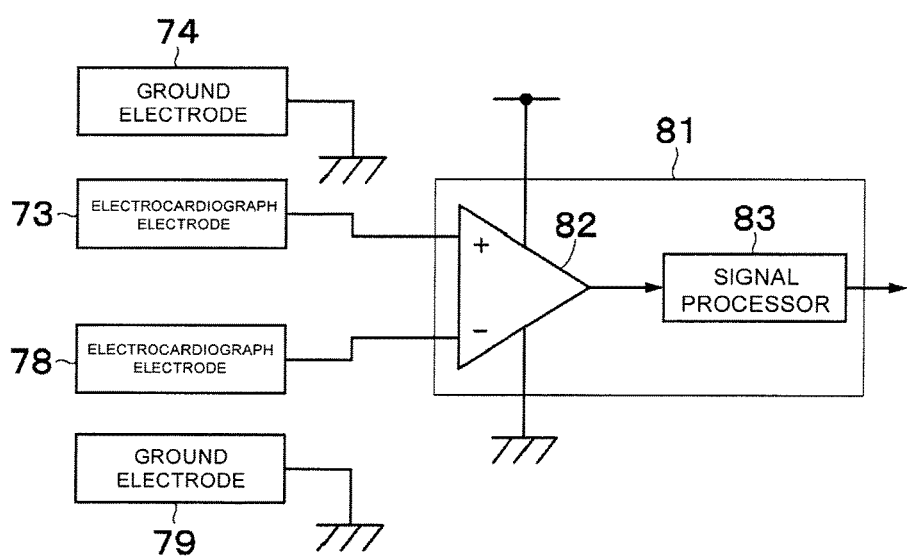
FIG. 19 is a circuit diagram illustrating an electrocardiograph-signal detector in FIG. 18.

As illustrated in FIGS. 18 and 19, a processing circuit 80 mainly includes a photoelectric-pulse-wave-signal detector 13, an electrocardiograph-signal detector 81, and an arithmetic processing unit 84. For example, the processing circuit 80 is provided in a game machine that is connected with both the left-hand and right-hand lever devices 72 and 75.

The electrocardiograph-signal detector 81 generates an electrocardiograph signal of a user. The electrocardiograph-signal detector 81 includes a differential amplifier 82 and a signal processor 83.

The differential amplifier 82 is formed of, for example, a differential amplifying circuit including an operational amplifier. Input terminals of the differential amplifier 82 are connected with the electrocardiograph electrodes 73 and 78. Wirings from the electrocardiograph electrodes 73 and 78 and the ground electrodes 74 and 79 are connected with the differential amplifier 82. Hence, the ground potential of the differential amplifier 82 is the same as the ground potential of the ground electrodes 74 and 79. The differential amplifier 82 generates an electrocardiograph signal (electrocardiogram signal) by executing differential amplification on electric signals according to the electrocardiograph signals output from the electrocardiograph electrodes 73 and 78. That is, the differential amplifier 82 generates an electrocardiograph signal by executing differential amplification on an electric signal detected from the palm P of the left hand LH of the user by the electrocardiograph electrode 73 and an electric signal detected from the palm P of the right hand RH of the user by the electrocardiograph electrode 78. The signal processor 83 formed of, for example, a filter circuit, executes noise removal and various signal processing on the electrocardiograph signal, and then the result is input to the arithmetic processing unit 84.

The arithmetic processing unit 84 is, for example, a central processing unit (CPU), and performs processing of extracting a photoelectric pulse wave signal from a light detection signal output from the light receiver 9 by using the photoelectric-pulse-wave-signal detector 13, similarly to the arithmetic processing unit 17 according to the first embodiment. Also, the arithmetic processing unit 84 generates living body information, such as an electrocardiogram, a heart rate (pulse rate), oxygen saturation, a pulse-wave propagation time, an acceleration pulse wave, and pulse fluctuation, based on the photoelectric pulse wave signal, and the electrocardiograph signal generated by the differential amplifier 82.

Thus, even with the sixth embodiment, effects and advantages similar to those of the first embodiment can be obtained. In particular, in the sixth embodiment, since the electrocardiograph electrodes 73 and 78 are provided, electrocardiograph signals can be measured by using the electrocardiograph electrodes 73 and 78. Hence, the photoelectric pulse wave signal and the electrocardiograph signal can be simultaneously stably measured. The various living body information can be generated on the basis of the photoelectric pulse wave signal and the electrocardiograph signal.

In this case, to stably measure the electrocardiograph signal, it is necessary to arrange the electrocardiograph electrode not at a frequently moving portion, but at a portion in a stable contact state. If the contact state is changed, noise is added, and the electrocardiograph signal is no longer stably measured. When the user holds the levers 4 and 77, the contact state of the fingers (in particular, the thumb F1 and the index finger F2) is frequently changed by the operation of the levers 4 and 77, and the trigger button 5. In contrast, the palm P stably contacts the electrocardiograph electrodes 73 and 78 provided at the levers 4 and 77. Accordingly, the electrocardiograph signals can be stably measured.

Also, for example, if a center portion M of the palm P is compressed, blood flow in a measurement portion S is blocked, and measurement of the photoelectric pulse wave signal becomes difficult. In contrast, the electrocardiograph signal cannot be stably measured if the contact state between the electrocardiograph electrodes 73 and 78 and the skin of the user is unstable. Owing to this, arrangement of the electrocardiograph electrodes 73 and 78 at positions at which the electrocardiograph electrodes 73 and 78 contact the center portion M or the wrist-side portion W of the palm P should be avoided, as positions at which the compression on the skin should be avoided with regard to the blockage of the blood flow.

Regarding these points, in this embodiment, the sensor unit 7 that measures the photoelectric pulse wave signal and the electrocardiograph electrodes 73 and 78 that measure the electrocardiograph signals are arranged at positions so as to contact a portion excluding the center portion M and the wrist-side portion W of the palm P. In addition, the electrocardiograph electrodes 73 and 78 are arranged at positions at which the electrocardiograph electrodes 73 and 78 stably contact the skin, such as the position at which the blood-flow blockage reducing part 18 is arranged. Accordingly, for example, as compared with a case in which the electrocardiograph electrodes 73 and 78 are arranged at positions so as to contact the center portion M or the wrist-side portion W of the palm P, the electrocardiograph electrodes 73 and 78 can stably contact the palm P of the user while the blockage of the blood flow in the measurement portion S is restricted. Consequently, the photoelectric pulse wave signal and the electrocardiograph signal can be simultaneously stably measured. Also, since noise, which is generated, for example, if a finger moves, is less superposed on the electrocardiograph signal, the electrocardiograph signal can be stably measured.

Further, the ground electrodes 74 and 79 are provided at the positions at which the ground electrodes 74 and 79 contact the hypothenar of the palm P. Owing to this, since the noise generated if the finger moves is less superposed on the electrocardiograph signal, the electrocardiograph signal can be stably measured. Also, since the ground potential is aligned with the user (living body), even if noise, such as commercial power noise, is mixed through the user, the electrocardiograph signal can be stably measured.

Figure 20:
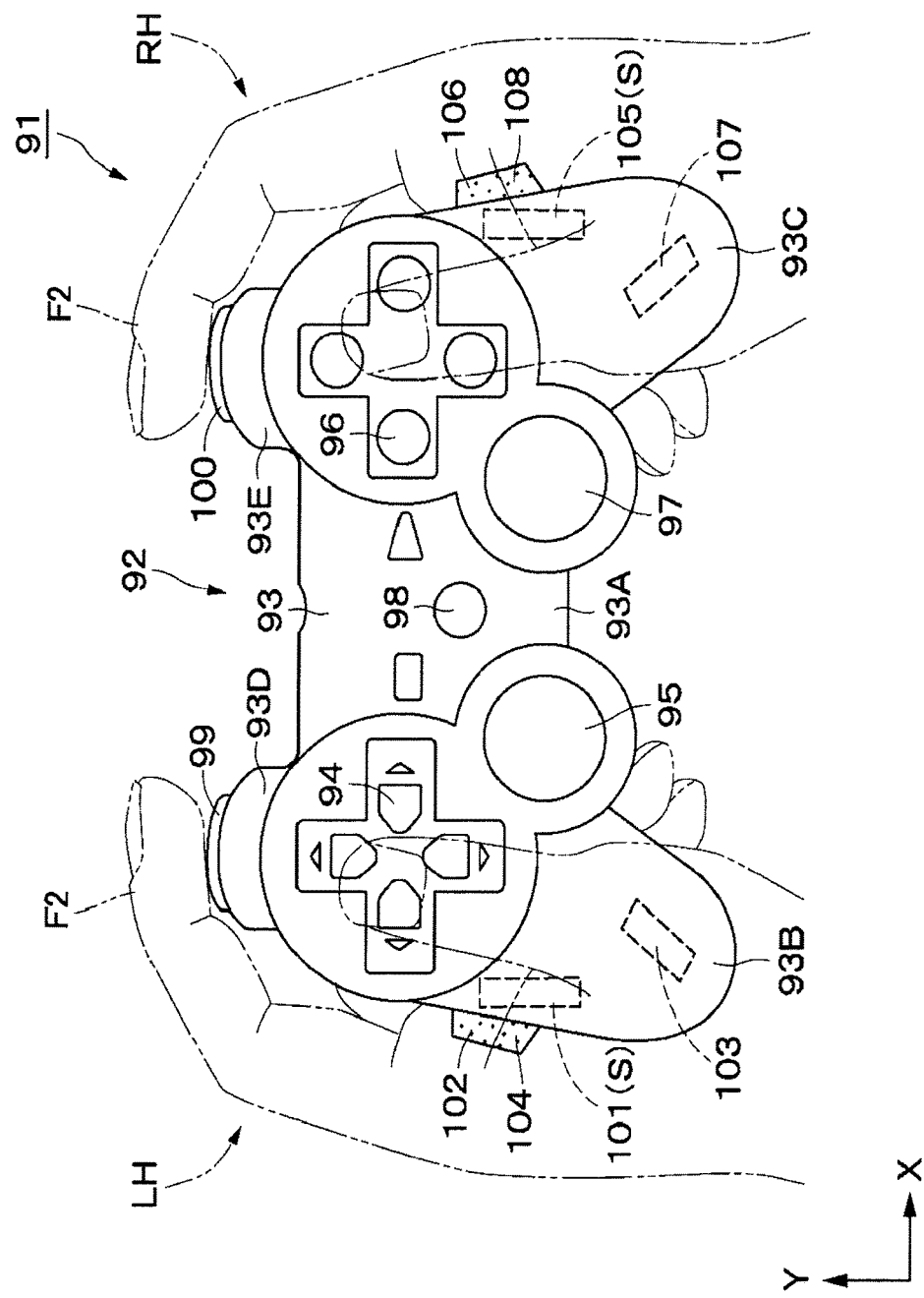
FIG. 20 is a plan view illustrating a pulse wave sensor device according to a seventh embodiment.
Figure 21:
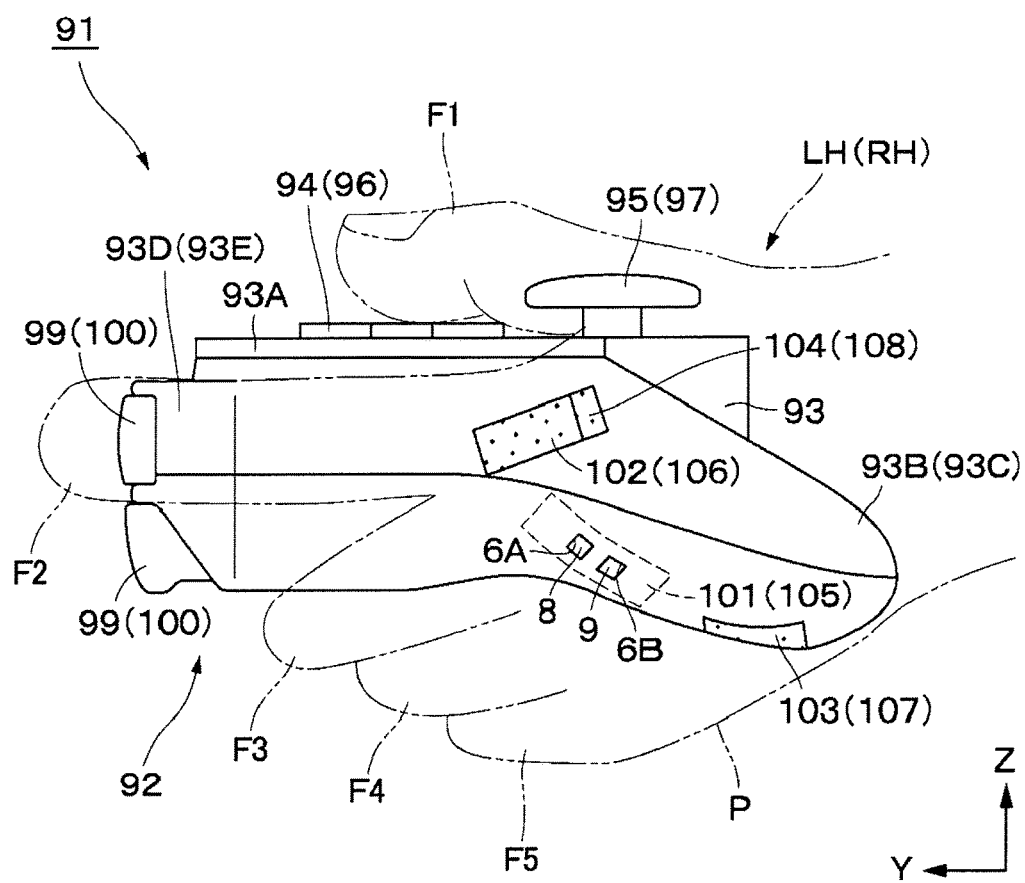
FIG. 21 is a side view from the left side of the pulse wave sensor device in FIG. 20.

Next, FIGS. 20 and 21 illustrate a seventh embodiment of the invention. A feature of this embodiment is a configuration in which a light emitter and a light receiver, as well as an electrocardiograph electrode are attached to a game controller. In this embodiment, the same reference sign is applied to the same component of the first embodiment, and the description is omitted.

A pulse wave sensor device 91 is applied to, for example, a game controller 92 serving as an operation device that operates an operation subject in a game screen.

The game controller 92 is formed substantially similarly to the game controller 32 according to the third embodiment. Hence, the game controller 92 includes a casing 93, buttons 94, 96, 98, 99, and 100, and analog input parts 95 and 97. Also, the casing 93 includes a body part 93A, left and right grip parts 93B and 93C, and left and right forward protruding parts 93D and 93E, and forms a sensor attachment body.

The casing 93 has a signal output circuit (not illustrated) therein. The signal output circuit outputs signals from the buttons 94, 96, 98, 99, and 100 and signals from the analog input parts 95 and 97. The game controller 92 is connected with, for example, a game machine or a computer by a wired method or a wireless method, and outputs a signal from the signal output circuit to the game machine etc., similarly to the lever device 2 according to the first embodiment.

The left grip part 93B has a substantially triangular shape and extends from the left side of the body part 93A obliquely rearward. The grip part 93B has a substantially elliptic cross section, and is gripped with the thumb F1 and the thenar, which is a base portion of the thumb F1, as well as the middle finger F3, the ring finger F4, and the little finger F5 of the left hand LH.

A sensor unit 101, which is substantially similar to the sensor unit 7 according to the first embodiment, is attached to the left side surface of the grip part 93B. The sensor unit 101 includes a light emitter 8 and a light receiver 9. The light emitter 8 and the light receiver 9 are arranged at positions close to the bottom surface of the grip part 93B, and are inserted into element openings 6A and 6B provided at the grip part 93B. Accordingly, when the user grips the grip part 93B with the left hand LH, the light emitter 8 and the light receiver 9 are arranged at, for example, a portion close to the bases of the middle finger F3, the ring finger F4, and the little finger F5, as a measurement portion S of the palm P of the left hand LH.

Also, a blood-flow blockage reducing part 102 protruding leftward is provided at the left side surface of the grip part 93B. The blood-flow blockage reducing part 102 is formed substantially similarly to the blood-flow blockage reducing part 18 according to the first embodiment, and is arranged above the light emitter 8 and the light receiver 9. Hence, when the user grips the game controller 92 with the left hand LH, the blood-flow blockage reducing part 102 contacts, for example, a portion between the index finger F2 and the middle finger F3, and the thumb F1, as a contact portion C of the palm P of the left hand LH.

An electrocardiograph electrode 103 for measuring an electrocardiograph signal is provided at a rear portion of the bottom surface of the grip part 93B. The electrocardiograph electrode 103 is arranged at, for example, a position so as to contact the hypothenar of the left hand LH when the grip part 93B is gripped with the left hand LH. Also, a ground electrode 104 connected with a ground potential is provided at the surface position and the peripheral position of the blood-flow blockage reducing part 102. The ground electrode 104 contacts, for example, a portion between the index finger F2 and the middle finger F3, and the thumb F1 of the palm P of the left hand LH.

Similarly, the right grip part 93C has a substantially triangular shape and extends from the right side of the body part 93A obliquely rearward. The right grip part 93C is gripped with the thumb F1 and the thenar, which is a base portion of the thumb F1, as well as the middle finger F3, the ring finger F4, and the little finger F5 of the right hand RH.

A sensor unit 105 and a blood-flow blockage reducing part 106 are provided at the right side surface of the grip part 93C, at positions left-right symmetric to the positions of the sensor unit 101 and the blood-flow blockage reducing part 102. Accordingly, when the user grips the grip part 93C with the right hand RH, the light emitter 8 and the light receiver 9 of the sensor unit 105 are arranged at, for example, a portion close to the bases of the middle finger F3, the ring finger F4, and the little finger F5, as the measurement portion S of the palm P of the right hand RH. At this time, the blood-flow blockage reducing part 106 provided at the right side surface of the grip part 93C contacts, for example, a portion between the index finger F2 and the middle finger F3, and the thumb F1, as a contact portion C of the palm P of the right hand RH.

Also, an electrocardiograph electrode 107 and a ground electrode 108 are provided at the right side surface of the grip part 93C, at positions left-right symmetric to the positions of the electrocardiograph electrode 103 and the ground electrode 104. In this case, the electrocardiograph electrode 107 contacts, for example, the hyperthenar of the palm P of the right hand RH, and the ground electrode 108 contacts, for example, the portion between the index finger F2 and the middle finger F3, and the thumb F1.

Thus, even with the seventh embodiment, effects and advantages similar to those of the first, third, and sixth embodiments can be obtained.

In the sixth embodiment, the electrocardiograph electrodes 73 and 78 are each arranged at the surface position of the blood-flow blockage reducing part 18, and each contact the portion between the index finger F2 and the middle finger F3, and the thumb F1. However, the invention is not limited thereto. The electrocardiograph electrode may be arranged at a position excluding a portion which causes the blood flow in the measurement portion S to be blocked, like the center portion M and the wrist-side portion W of the palm P, and at a position at which the contact state with the skin becomes stable. Hence, the electrocardiograph electrode may be arranged at a position so as to contact, for example, a portion between the index finger and the thumb, a position so as to contact the hypothenar of the palm, or a plurality of such positions.

Also, in the seventh embodiment, the electrocardiograph electrodes 103 and 107 are each arranged at the position so as to contact the hypothenar of the palm P. However, the electrocardiograph electrodes 103 and 107 may be each arranged at a position so as to contact the surface position of the blood-flow blockage reducing part 102, 106, a position so as to contact a portion between the index finger and the thumb of the palm, or a plurality of such positions. Further, when the user holds the casing 93 with both hands, the ring fingers F4 and the little fingers F5 relatively less move, and stably contact the grip parts 93B and 93C. Accordingly, the electrocardiograph electrode may be arranged at a position of the grip part 93B, 93C so as to contact the ring finger F4 and/or the little finger F5.

Also, in any of the sixth and seventh embodiments, the single ground electrode 74, 104 that contacts the left hand LH, and the single ground electrode 79, 108 that contacts the right hand RH are provided. However, the invention is not limited thereto. A plurality of ground electrodes that contact the left hand LH, and a plurality of ground electrodes that contact the right hand RH may be provided. Further, one of the ground electrodes that contact the left hand LH and the right hand RH may be omitted, and all ground electrodes that contact both hands may be omitted.

Figure 22:
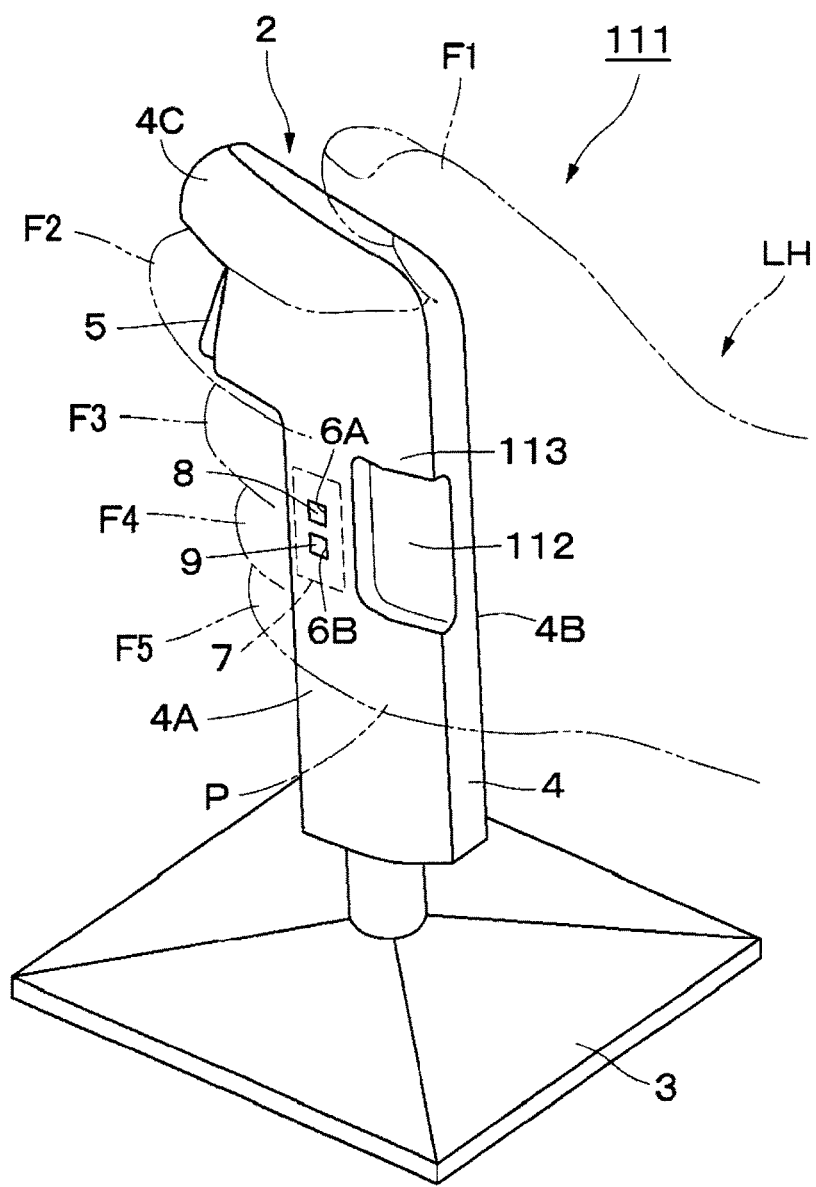
FIG. 22 is a perspective view from the left side of a plus wave sensor device according to a modification.

Also, in any of the first to third, sixth, and seventh embodiments, the blood-flow blockage reducing part 18, 42, 44, 102, 106 protrudes from the lever 4, 77 or the casing 33, 93. However, the invention is not limited thereto. Like a pulse wave sensor device 111 according to a modification illustrated in FIG. 22, a lever 4 may have a recess part 112 that is recessed with respect to a left side surface 4A, at a position corresponding to a center portion M and a wrist-side portion W of a palm P, and a peripheral portion of the recess part 112 may form a blood-flow blockage reducing part 113. Accordingly, since a step is formed between the blood-flow blockage reducing part 113 and the recess part 112, even when the user strongly grips the lever 4, compression acting on the center portion M and the wrist-side portion W of the palm P can be reduced. This configuration may be applied also to any of the second, third, sixth, and seventh embodiments.

In any of the first, second, and sixth embodiments, the lever 4, 25, 77 is supported by the pedestal 3, 24, 76. However, if a lever has a sensor that detects various motions and displacements, such as an angular velocity sensor and an acceleration sensor, the lever does not have to be attached to the pedestal, and the invention may be applied to the lever without the pedestal.

In any of the fourth and fifth embodiments, the pulse wave sensor device 51, 61 that is worn on the left hand LH is exemplified. However, a pulse wave sensor device that is worn on the right hand RH may be configured similarly.

In any of the fourth and fifth embodiments, the fixing tool 52, 62 is formed by using a bandage etc. However, a grove that covers also fingertips may be used. Alternatively, a seal that can adhere to and be removed from the palm P may be used.

In any of the fourth and fifth embodiments, since the light emitter 8 and the light receiver 9 are provided in the sensor casing 53, 63, the sensor casing 53, 63 serving as the blood-flow blockage reducing part contacts the same portion as the measurement portion S of the palm P. However, the invention is not limited thereto. Like any of the first to third embodiments, the blood-flow blockage reducing part may be provided separately from the sensor casing, and the blood-flow blockage reducing part may contact a portion different from the measurement portion S of the palm P. For example, in the fifth embodiment, a blood-flow blockage reducing part that contacts a portion between the index finger F2 and the middle finger F3, and the thumb F1 of the palm P may be separately provided in addition to the sensor casing 63. Accordingly, the pulse wave can be further stably detected.

In any of the first to third, sixth, and seventh embodiments, the measurement portion S that contacts the light emitter 8 and the light receiver 9 is different from the contact portion C that contacts the blood-flow blockage reducing part 18. However, the invention is not limited thereto, and the measurement portion S may be the same as the contact portion C. In this case, for example, like any of the fourth and fifth embodiments, the sensor casing may protrude from the peripheral portion to the palm P, the light emitter 8 and the light receiver 9 may be provided in the sensor casing, and the sensor casing may function as the blood-flow blockage reducing part.

In any of the first to seventh embodiments, the single light emitter 8 is used. However, a plurality of light emitters that emit detection light rays with different wavelength ranges may be provided.

In any of the first to third, sixth, and seventh embodiments, the example, in which the pulse wave sensor device 1, 21, 31, 71, 91 is applied to the lever device 2, 22, 23, 72, 75, or the game controller 32, 92. For example the pulse wave sensor may be applied to any configuration gripped with a hand, such as a steering wheel of a vehicle, a handle of a bicycle or a motorcycle, an umbrella, or a stick.

In the third embodiment, the game controller 32 is exemplified as an operation device that is operated with a fingertip. However, the operation device operated with a fingertip may be a remote control device that operates a television monitor, for example.

In any of the first, second, third, fifth, sixth, and seventh embodiments, the measurement portion S is set at the position close to the bases of the middle finger F3, the ring finger F4, and the little finger F5 of the palm P, and in the fourth embodiment, the measurement portion S is set at the hypothenar HE of the palm P. However, the invention is not limited thereto. For example, the measurement portion S may be set at a portion close to the bases of the thumb F1 and/or the index finger F2 of the palm P, or at the thenar of the palm P, as a portion excluding the center portion M and the wrist-side portion W of the palm P.

REFERENCE SIGNS LIST 1, 21, 31, 51, 61, 71, 91, 111 pulse wave sensor device
2, 22, 23, 72, 75 lever device
4, 25, 77 lever
8 light emitter
9 light receiver
18, 42, 44, 102, 106, 113 blood-flow blockage reducing part
32, 92 game controller (operation device)
33, 93 casing
52, 62 fixing tool
53, 63 sensor casing (blood-flow blockage reducing part)
73, 78, 103, 107 electrocardiograph electrode
74, 79, 104, 108 ground electrode
112 recess part

The invention claimed is:

1. A pulse wave sensor device comprising:
a device body having a contoured shape adapted to be gripped by a hand of a user;
a measurement sensor disposed on the device body and having:
 a light emitter configured to emit light to a measurement location on a palm of the hand when the user grips the device body, and a
 light receiver configured to detect light reflected by the measurement location; and
a protruding member that extends from the device body and that is adapted to contact a contact location of the palm when the user grips the device body, with the contact location not being a center portion or a wrist-side portion of the palm,
wherein the protruding member is adapted to reduce compression at the center portion and the wrist-side portion of the palm of the hand, which are upstream of blood flow in the hand at the measurement location,
wherein the protruding member is step shaped with a planar step surface that contacts the contact location of the palm when the user grips the device body and includes side surfaces that extend at an angle from the planar step surface to the device body to create a gap between the device body and a portion of the palm different than the contact location and different than the measurement location, such that the protruding member reduces the blockage of blood flow in the hand at the measurement location.

2. The pulse wave sensor device according to claim 1, wherein the measurement sensor is disposed on the device body at a same position from where the protruding member extends from the device body.

3. The pulse wave sensor device according to claim 1, wherein the measurement sensor is disposed on the device body at a different position where the protruding member extends from the device body.

4. The pulse wave sensor device according to claim 1, wherein the measurement sensor is disposed at a position in the device body, such that when the user grips the device body, the measurement location of the hand is adjacent to a base of a finger of the hand.

5. The pulse wave sensor device according to claim 4, wherein the device body comprises a lever and the protruding member extends from the device body and is adapted to contact the contact location that is between an index finger and a middle finger, and a thumb of the palm when the user grips the device body.

6. The pulse wave sensor device according to claim 5, wherein the lever comprises a left-hand lever and a right-hand lever, and the measurement sensor comprises a pair of measurement sensors that are disposed on the left-hand lever and the right-hand lever at different respective positions on the respective levers.

7. The pulse wave sensor device according to claim 1, wherein the device body comprises an operation device operable by a fingertip of the hand when the user grips the device body, and
wherein the measurement sensor is attached to the operation device.

8. The pulse wave sensor device according to claim 7, wherein the protruding member is adapted to contact the contact location that is between an index finger and a middle finger, and a thumb of the palm when the user grips the device body.

9. The pulse wave sensor device according to claim 1, wherein the measurement location on the hand is a hypothenar of the palm of the hand when the user grips the device body.

10. The pulse wave sensor device according to claim 1, further comprising an electrocardiograph electrode adapted to contact the hand of the user when the user grips the device body, the electrocardiograph electrode being configured to measure an electrocardiograph signal of the user.

11. The pulse wave sensor device according to claim 10, wherein the electrocardiograph electrode is adapted to contact a surface of the hand of the user when the user grips the device body at a position of the contact location of the palm or at a position of the hand between an index finger and a thumb of the hand, or at a position of a hypothenar of the palm of the hand.

12. The pulse wave sensor device according to claim 11, further comprising a ground electrode adapted to contact the hand at a position different from the contact position of the electrocardiograph electrode.

13. The pulse wave sensor device according to claim 12, wherein the ground electrode is adapted to contact a surface of the hand of the user when the user grips the device body at a position of the contact location of the palm or at a position of the hand between an index finger and a thumb of the hand, or at a position of a hypothenar of the hand.

14. The pulse wave sensor device according to claim 12, wherein the measurement sensor further comprises a light shield disposed between the light emitter and the light receiver.

15. A pulse wave sensor device comprising:
a device body extending in a first direction and having a contoured shape adapted to be gripped by a hand of a user;
a guide protrusion extending from a top of the device body;
a measurement sensor disposed on the device body and having:
a light emitter configured to emit light to a measurement location on the hand when the user grips the device body, and
a light receiver configured to detect light reflected by the measurement location; and
a protruding member that extends from the device body and that is adapted to contact a contact location of the hand when the user grips the device body, such that the protruding member reduces blockage of blood flow in the hand at the measurement location,
wherein the protruding member is disposed at a height that is lower than a height of the guide protrusion relative to the first direction, and
wherein the measurement sensor is disposed at a height that is lower than the height of the protruding member relative to the first direction
wherein the guide protrusion is configured to guide the hand of the user when the user grips the device body such that the protruding member contacts the contact location of the hand.

* * * * *